US012558144B2

(12) United States Patent (10) Patent No.: US 12,558,144 B2

Forsyth et al. (45) Date of Patent: Feb. 24, 2026

(54) WAVEFORM GENERATOR AND CONTROL FOR SELECTIVE CELL ABLATION

(71) Applicant: BOSTON SCIENTIFIC SCIMED, INC., Maple Grove, MN (US)

(72) Inventors: Bruce R. Forsyth, Hanover, MN (US); Larry D. Canady, Jr., Ham Lake, MN (US); Jonathan Tyler Gorzycki, Blaine, MN (US); Timothy A. Ostroot, Cokato, MN (US); Hong Cao, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1523 days.

(21) Appl. No.: 16/818,035

(22) Filed: Mar. 13, 2020

(65) Prior Publication Data

US 2020/0289185 A1 Sep. 17, 2020

Related U.S. Application Data

(60) Provisional application No. 62/819,101, filed on Mar. 15, 2019.

(51) Int. Cl.
| | |
|---|---|
| *A61B 18/12* | (2006.01) |
| *A61B 5/00* | (2006.01) |
| *A61B 18/00* | (2006.01) |

(52) U.S. Cl.
CPC ........ *A61B 18/1206* (2013.01); *A61B 5/4519* (2013.01); *A61B 2018/00577* (2013.01); *A61B 2018/0075* (2013.01)

(58) Field of Classification Search
None
See application file for complete search history.

(56) References Cited

U.S. PATENT DOCUMENTS

| | | |
|---|---|---|
| 5,019,034 A | 5/1991 | Weaver et al. |
| 5,370,675 A | 12/1994 | Edwards et al. |
| 5,718,246 A | 2/1998 | Vona |
| 5,855,576 A | 1/1999 | Leveen et al. |
| 5,863,290 A | 1/1999 | Gough et al. |
| 6,010,613 A | 1/2000 | Walters et al. |

(Continued)

FOREIGN PATENT DOCUMENTS

| | | |
|---|---|---|
| JP | H11346436 A | 12/1999 |
| JP | 2001157685 A | 6/2001 |

(Continued)

OTHER PUBLICATIONS

StarBurst XL RFA Electrodes, Angiodynamics Inc. 2013. 2 pages.

(Continued)

*Primary Examiner* — Joanne M Rodden
*Assistant Examiner* — Nora W Rhodes
(74) *Attorney, Agent, or Firm* — Seager, Tufte & Wickhem LLP

(57) ABSTRACT

Methods and devices for performing ablation. In some examples an ablation delivery system is configured to allow separate voltage levels of a capacitor stack to be accessed for use in therapy delivery. Ablation therapy systems switchable between current and voltage controlled output are described. Methods of treating a patient using adjustable interphase or interpulse delay are disclosed as well.

20 Claims, 19 Drawing Sheets

(56) References Cited

U.S. PATENT DOCUMENTS

| | | | |
|---|---|---|---|
| 6,041,252 A | 3/2000 | Walker et al. | |
| 6,043,066 A | 3/2000 | Mangano et al. | |
| 6,278,895 B1 | 8/2001 | Bernard | |
| 6,326,177 B1 | 12/2001 | Schoenbach et al. | |
| 6,387,671 B1 | 5/2002 | Rubinsky et al. | |
| 6,428,534 B1 | 8/2002 | Joye et al. | |
| 6,638,277 B2 | 10/2003 | Schaefer et al. | |
| 6,714,816 B1 | 3/2004 | Heller et al. | |
| 6,912,471 B2 | 6/2005 | Heigl et al. | |
| 6,952,608 B2 | 10/2005 | Ostroff | |
| 6,994,706 B2 | 2/2006 | Chornenky et al. | |
| 7,245,963 B2 | 7/2007 | Draghia-Akli et al. | |
| 7,306,595 B2 | 12/2007 | Ostrovsky et al. | |
| 7,306,940 B2 | 12/2007 | Miklavcic et al. | |
| 7,416,549 B2 | 8/2008 | Young et al. | |
| 7,456,012 B2 | 11/2008 | Ryttsn et al. | |
| 7,794,458 B2 | 9/2010 | Mcintyre et al. | |
| 7,799,022 B2 | 9/2010 | Fernald et al. | |
| 7,850,681 B2 | 12/2010 | Lafontaine | |
| 8,014,854 B2 | 9/2011 | Schroeppel et al. | |
| 8,048,067 B2 | 11/2011 | Davalos et al. | |
| 8,114,070 B2 | 2/2012 | Rubinsky et al. | |
| 8,152,801 B2 | 4/2012 | Goldberg et al. | |
| 8,211,104 B2 | 7/2012 | Mccullagh et al. | |
| 8,251,986 B2 | 8/2012 | Chornenky et al. | |
| 8,282,631 B2 | 10/2012 | Davalos et al. | |
| 8,465,484 B2 | 6/2013 | Davalos et al. | |
| 8,540,710 B2 | 9/2013 | Johnson et al. | |
| 8,603,087 B2 | 12/2013 | Rubinsky et al. | |
| 8,647,338 B2 | 2/2014 | Chornenky et al. | |
| 8,801,709 B2 | 8/2014 | Prakash et al. | |
| 8,915,911 B2 | 12/2014 | Azure | |
| 8,920,416 B2 | 12/2014 | Pham et al. | |
| 8,926,606 B2 | 1/2015 | Davalos et al. | |
| 9,005,189 B2 | 4/2015 | Davalos et al. | |
| 9,168,096 B2 | 10/2015 | Kreindel | |
| 9,987,081 B1 | 6/2018 | Bowers et al. | |
| 10,105,172 B2 | 10/2018 | Johnson et al. | |
| 10,154,869 B2 | 12/2018 | Onik et al. | |
| 10,864,385 B2 * | 12/2020 | Barthe | A61B 8/461 |
| 11,045,648 B2 | 6/2021 | Dewitt et al. | |
| 2001/0044596 A1 | 11/2001 | Jaafar | |
| 2002/0107515 A1 | 8/2002 | Edwards et al. | |
| 2002/0115991 A1 | 8/2002 | Edwards | |
| 2003/0009110 A1 | 1/2003 | Tu et al. | |
| 2004/0186468 A1 | 9/2004 | Edwards | |
| 2005/0267467 A1 | 12/2005 | Paul et al. | |
| 2006/0142801 A1 | 6/2006 | Demarais et al. | |
| 2006/0293730 A1 | 12/2006 | Rubinsky et al. | |
| 2007/0025919 A1 | 2/2007 | Deem et al. | |
| 2008/0275445 A1 | 11/2008 | Kelly et al. | |
| 2009/0247933 A1 | 10/2009 | Maor et al. | |
| 2009/0254148 A1 | 10/2009 | Borgens et al. | |
| 2009/0326638 A1 | 12/2009 | Atanasoka et al. | |
| 2010/0023004 A1 | 1/2010 | Francischelli et al. | |
| 2010/0261994 A1 | 10/2010 | Davalos et al. | |
| 2010/0280371 A1 * | 11/2010 | Lacoste | H02K 47/04 |
| | | | 600/437 |
| 2011/0238057 A1 | 9/2011 | Moss et al. | |
| 2012/0053403 A1 | 3/2012 | Ducharme et al. | |
| 2012/0197356 A1 | 8/2012 | Wei et al. | |
| 2012/0310230 A1 | 12/2012 | Willis | |
| 2012/0330299 A1 | 12/2012 | Webster et al. | |
| 2013/0030277 A1 * | 1/2013 | Fahey | A61N 1/0452 |
| | | | 607/48 |
| 2013/0184702 A1 | 7/2013 | Neal, II et al. | |
| 2014/0121663 A1 | 5/2014 | Pearson et al. | |
| 2014/0128859 A1 | 5/2014 | Lee | |
| 2014/0128936 A1 | 5/2014 | Laufer et al. | |
| 2016/0113709 A1 | 4/2016 | Maor | |
| 2016/0199661 A1 | 7/2016 | Willard et al. | |
| 2017/0035499 A1 | 2/2017 | Stewart | |
| 2017/0105793 A1 | 4/2017 | Cao et al. | |
| 2017/0245928 A1 | 8/2017 | Xiao et al. | |
| 2018/0056066 A1 * | 3/2018 | Boggs | A61N 1/36017 |
| 2018/0250508 A1 | 9/2018 | Howard | |
| 2018/0272124 A1 | 9/2018 | Kibler et al. | |
| 2018/0303543 A1 | 10/2018 | Stewart et al. | |
| 2019/0143106 A1 | 5/2019 | Dewitt et al. | |
| 2019/0223943 A1 | 7/2019 | Forsyth et al. | |
| 2019/0274746 A1 * | 9/2019 | Toth | A61K 9/06 |
| 2020/0129230 A1 | 4/2020 | Forsyth et al. | |
| 2020/0138506 A1 * | 5/2020 | Fraasch | A61B 18/1206 |
| 2020/0155227 A1 | 5/2020 | Cao et al. | |
| 2020/0289185 A1 | 9/2020 | Forsyth et al. | |
| 2020/0289188 A1 | 9/2020 | Forsyth et al. | |
| 2020/0289827 A1 | 9/2020 | Forsyth et al. | |

FOREIGN PATENT DOCUMENTS

| | | | |
|---|---|---|---|
| WO | 2015021113 A1 | 2/2015 | |
| WO | 2017119934 A1 | 7/2017 | |
| WO | 2018200800 A1 | 11/2018 | |

OTHER PUBLICATIONS

StarBurst Talon Infusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", PLOS ONE, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Jun. 26, 2020 for International Application No. PCT/US2020/022578.

International Seatrch Report and Written pinion dated Jul. 7, 2020 for International Application No. PCT/US2020/022571.

International Search Report and Written Opinion dated Jul. 2, 2020 for International Application No. PCT/US2020/022582.

* cited by examiner

FIG. 13C

WAVEFORM GENERATOR AND CONTROL FOR SELECTIVE CELL ABLATION

CROSS-REFERENCE TO RELATED PATENT DOCUMENTS

This application claims the benefit of and priority to US Provisional Patent Application 62/819,101, filed on Mar. 15, 2019 and titled WAVEFORM GENERATOR AND CONTROL FOR SELECTIVE CELL ABLATION, this disclosure of which is incorporated by reference. This application is also related to U.S. Provisional Patent Application 62/819,120, filed on Mar. 15, 2019 and titled TIME MULTIPLEXED WAVEFORM FOR SELECTIVE CELL ABLATION, and US Provisional Patent Application 62/819,135, filed on Mar. 15, 2019 and titled SPATIALLY MULTIPLEXED WAVEFORM FOR SELECTIVE CELL ABLATION, the disclosures of which are incorporated herein by reference.

BACKGROUND

Removal or destruction of diseased tissue is a goal of many cancer treatment methods. Tumors may be surgically removed, however, less invasive approaches garner much attention. Tissue ablation is a minimally invasive method of destroying undesirable tissue in the body. Ablation may be thermal or non-thermal.

Thermal ablation either adds or removes heat to destroy undesirable cells. For example, cryoablation kills cells by freezing of the extracellular compartment resulting in cell dehydration beginning at −15 C with membrane rupture occurring at colder temperatures. Cryoablation is known to (beneficially) stimulate an antitumor immune response in the patient.

Heat-based thermal ablation adds heat to destroy tissue. Radio-frequency (RF) thermal, microwave and high intensity focused ultrasound ablation can each be used to raise localized tissue temperatures well above the body's normal 37 degrees C. For example, RF thermal ablation uses a high frequency electric field to induce vibrations in the cell membrane that are converted to heat by friction. Cell death occurs in as little as 30 seconds once the cell temperature reaches 50 degrees C., while at higher temperatures cell death is instantaneous. Heat based ablation, however, may not prompt the desirable immune response associated with cryoablation.

Thermal ablation techniques using heat or cold each suffer from the drawback that they have little or no ability to spare normal structures in the treatment zone. Collateral injury to vascular, neural and other structures is undesirable. For this reason, various researchers have explored non-thermal ablation as well.

Non-thermal ablation techniques include electro-chemotherapy, reversible electroporation, and irreversible electroporation. Electroporation refers to a phenomenon in which the plasma membrane of a cell exposed to high voltage pulsed electric fields becomes temporarily permeable due to destabilization of the lipid bilayer. Pores then form, at least temporarily. Electro-chemotherapy combines pore formation with the introduction of chemicals that cause cell death. Because the chemical molecules used are large, only cells subject to the electric fields will absorb the chemical material and subsequently die, making for useful selectivity in the treatment zone. Irreversible electroporation (IRE) omits the chemicals, and instead uses the electric fields, usually with increased amplitude, to expand pores in the cell membrane beyond the point of recovery, causing cell death for want of a patent cell membrane. The spatial characteristics of the applied field control which cells and tissue will be affected, allowing for better selectivity in the treatment zone than with thermal techniques.

One challenge with the electrical (whether thermal or not) ablation techniques is that of local muscle stimulation. A monophasic waveform is thought to provide better results for IRE in terms of causing certain cell death. However, monophasic waveforms tend to cause muscle stimulation, requiring the use of a paralytic to facilitate surgery, among other problems. A biphasic waveform avoids the muscle stimulation, but may not be as effective at the same energy level and/or amplitude as the monophasic waveform. Simply raising power to make the biphasic waveform more effective runs the risk of causing thermal ablation. Enhancements and alternatives to the state of the art are desired to allow a waveform to be used that is as effective as monophasic stimulus for IRE, while avoiding muscle stimulation and thus obtaining the benefits of both monophasic and biphasic therapy.

Overview

The present inventors have recognized, among other things, that a problem to be solved is the provision of ablation therapy that combines high efficacy and tissue selectivity while avoiding muscle stimulation. A number of examples shown below provide illustrative signal generators, systems and methods directed to such improvements.

A first non-limiting example takes the form of a device for generating energy for use in the electrical ablation of tissue comprising a voltage source; a capacitor bank having at least a first capacitor and one or more additional capacitors; and an output stage coupling the capacitor bank to a plurality of output nodes, the output stage comprising: a power selector switch pair coupled to the capacitor stack to enable a first output to be defined including the first capacitor and at least one of the one or more additional capacitors, or a second output excluding the first capacitor and including at least one of the one or more additional capacitors, such that the first output is at a higher voltage than the second output; and a plurality of electrode selector switch pairs each associated with one of the plurality of output nodes, each electrode selector switch pair including a high side switch coupled to the power selector switch pair and a low side switch coupled to reference.

Additionally or alternatively to the first non-limiting example, the device may further comprise a feedback circuit coupled to the plurality of output nodes, the feedback circuit comprising one or more current sensors for sensing and quantifying current through one or more output nodes, and a control node coupled to the feedback circuit, the power selector switch pairs and the plurality of electrode selector switch pairs to use the one or more current sensors to control the electrical ablation. Additionally or alternatively the feedback circuit may be configured to detect peak current of output to prevent damage to device componentry. Additionally or alternatively the feedback circuit may be configured to detect average current of output to determine characteristics of delivered therapy.

Additionally or alternatively to the first non-limiting example, the device may further comprise a feedback circuit coupled to the plurality of output nodes, the feedback circuit comprising one or more voltage sensors for sensing and quantifying voltage at one or more output nodes, and a control node coupled to the feedback circuit, the power selector switch pairs, and the plurality of electrode selector switch pairs to use the one or more voltage sensors to control the electrical ablation.

Additionally or alternatively to the first non-limiting example, the device may further comprise a feedback circuit comprising one or more voltage and/or current sensors for monitoring impedance to track tissue characteristics during therapy delivery.

A second non-limiting example takes the form of a device for generating energy for use in the electrical ablation of tissue comprising: a voltage source; a capacitor bank having at least a first capacitor and one or more additional capacitors, the capacitor bank accessible at a plurality of locations to operate as a plurality of output sources; and an output stage coupling the capacitor bank to a plurality of output nodes, the output stage comprising: a plurality of power selector switches coupled to the capacitor stack at the plurality of locations, the plurality of power selector switches allowing independent and simultaneous access to the capacitor bank to derive a plurality of outputs at the same or different voltage levels; and a plurality of electrode selector switch pairs each associated with one of the plurality of output nodes, each electrode selector switch pair including a high side switch coupled to the power selector switch pair and a low side switch coupled to reference.

Additionally or alternatively to the second non-limiting example, the device may further comprise a feedback circuit coupled to the plurality of output nodes, the feedback circuit comprising one or more current sensors for sensing and quantifying current through one or more output nodes, and a control node coupled to the feedback circuit, the power selector switch pairs and the plurality of electrode selector switch pairs to use the one or more current sensors to control the electrical ablation.

Additionally or alternatively to the second non-limiting example, the device may further comprise a feedback circuit coupled to the plurality of output nodes, the feedback circuit comprising one or more voltage sensors for sensing and quantifying current at one or more output nodes, and a control node coupled to the feedback circuit, the power selector switch pairs, and the plurality of electrode selector switch pairs to use the one or more voltage sensors to control the electrical ablation.

Additionally or alternatively to the second non-limiting example, the device may further comprise a feedback circuit comprising one or more voltage and/or current sensors for monitoring impedance to track tissue characteristics during therapy delivery.

Additionally or alternatively to the first or second non-limiting examples, the output stage may define a plurality of paths from the capacitor bank to the output nodes, wherein at least one path comprises a current controlling circuit switchable into and out of the path, wherein switching one of the current controlling circuits into a path configures the device to use a constant current output.

Additionally or alternatively to the first or second non-limiting examples, the output stage may define a plurality of paths from the output nodes to the reference, wherein at least one path comprises a current controlling circuit switchable into and out of the path, wherein switching one of the current controlling circuits into a path configures the device to use a constant current output.

Additionally or alternatively to the first or second non-limiting examples, the control circuitry may be configured to provide a constant power output or, alternatively, a constant voltage output.

Another example takes the form of a system for ablating tissue comprising a device as in either the first or second non-limiting examples, and a probe for inserting into or placing in contact with or near tissue to be ablated.

A third illustrative and non-limiting example takes the form of method of treating a patient using an ablation therapy comprises setting output parameters for a biphasic electrical output comprising a first phase of a first polarity and a second phase of a second polarity opposite the first polarity, with an interpulse period defined between the first and second phases; a) delivering the biphasic electrical output to the patient using the output parameters and observing whether a muscle response occurs; b) if no muscle response is observed, modifying the output parameters by extending the interpulse period; repeating steps a) and b) until a muscle response is observed or until a predefined maximum interpulse period is used; and if a muscle response is observed, setting a therapeutic interpulse period as either a fraction of or a reduction of the interpulse period at which muscle response is observed; or if the maximum interpulse period is used, setting the therapeutic interpulse period at the maximum interpulse period; and delivering therapy to the patient using a set of therapy parameters including the therapeutic interpulse period.

A fourth illustrative and non-limiting example takes the form of a method of treating a patient using an ablation therapy comprises setting output parameters for an electrical output having a pulse width and amplitude; delivering the electrical output to the patient using the output parameters; observing whether a muscle response occurs in response to the delivered output; and one of: a) if no muscle response is observed, modifying the output parameters by increasing at least one of pulse width or amplitude of the electrical output; b) if a muscle response is observed, modifying the output parameters by decreasing at least one of pulse width or amplitude the electrical circuit; and again delivering the electrical output to the patient, using output parameters as modified in one of steps a) or b).

A fifth illustrative and non-limiting example takes the form of a method of treating a patient using an ablation therapy comprises: setting output parameters for a biphasic electrical output comprising a first phase of a first polarity and a second phase of a second polarity opposite the first polarity, with an interpulse period defined between the first and second phases; delivering the biphasic electrical output to the patient using the output parameters; observing whether a muscle response occurs; a) if no muscle response is observed, modifying the output parameters by extending the interpulse period; b) if a muscle response is observed, modifying the output parameters by reducing the interpulse period; and again delivering the biphasic electrical output to the patient using the output parameters as modified in one of steps a) and b).

A sixth illustrative and non-limiting example takes the form of a method of treating a patient using an ablation therapy comprising: setting output parameters for a biphasic electrical output comprising a first phase of a first polarity and a second phase of a second polarity opposite the first polarity, with an interpulse period defined between the first and second phases; delivering the biphasic electrical output to the patient using the output parameters; observing whether a muscle response occurs; determining that no muscle response occurs and modifying the output parameters by extending the interpulse period; and again delivering the biphasic electrical output to the patient using the output parameters with the extended interpulse period.

A seventh illustrative and non-limiting example takes the form of a method of treating a patient using an ablation therapy comprising: setting output parameters for a biphasic electrical output comprising a first phase of a first polarity and a second phase of a second polarity opposite the first polarity, with an interpulse period defined between the first and second phases; delivering the biphasic electrical output to the patient using the output parameters; observing whether a muscle response occurs; determining that a muscle response occurred and modifying the output parameters by reducing the interpulse period; and again delivering the biphasic electrical output to the patient using the output parameters with the reduced interpulse period.

Additionally or alternatively to the third to seventh non-limiting examples, the step of observing whether a muscle response occurs may be performed by a system user visually observing whether one of visible motion or migration of therapy probe occurs in response to the delivered biphasic electrical output.

Additionally or alternatively to the third to seventh non-limiting examples, the step of observing whether a muscle response occurs may be performed by monitoring an output of an accelerometer placed in or on the patient.

Additionally or alternatively to the third to seventh non-limiting examples, the step of observing whether a muscle response occurs may include sensing myopotentials of muscle tissue of the patient.

Additionally or alternatively to the third to seventh non-limiting examples, the step of observing whether a muscle response occurs may comprise obtaining a subjective feedback from the patient.

An eighth non-limiting example takes the form of a method of delivering an ablation therapy to a patient comprises delivering a therapy pulse train within a predetermined period of time as follows: delivering a first pulse having first voltage and first duration; sensing current during the first pulse; delivering a second pulse having second voltage and duration, wherein the first voltage does not equal the second voltage, and the first duration does not equal the second duration, but the product of the first voltage and first duration is substantially equal to the product of the second voltage and the second duration; sensing current during the second pulse; determining that a quantity of charge delivered during the first pulse is not equal to a quantity of charge delivered during the second pulse; and delivering at least one additional pulse to remove charge imbalance caused by difference between the quantity of charge of the first pulse and the quantity of charge of the second pulse, before expiration of the predetermined period of time.

Additionally or alternatively to the eighth non-limiting example, the at least one additional pulse may be a voltage controlled pulse having a third voltage and a third duration calculated by determining an impedance encountered by at least one of the first and second pulses.

Additionally or alternatively to the eighth non-limiting example, the at least one additional pulse may be a current controlled pulse, while the first and second pulses are voltage controlled pulses.

A ninth illustrative and non-limiting example takes the form of a device for generating energy for use in the electrical ablation of tissue comprising: a voltage source; a capacitor bank for storing energy from the voltage source to be used in delivering ablation energy; voltage conversion circuitry to deliver energy from the voltage source to the capacitor bank at a higher voltage than the voltage source can provide; an output stage coupling the capacitor bank to a plurality of output nodes; sensing circuitry for receiving a sensed signal from a probe adapted for use with the device; and a control circuit configured to control the capacitor bank, voltage conversion circuitry, and output stage, using feedback from the sensing circuitry; wherein the control circuit is configured to perform a method as in any of the third to eighth non-limiting examples.

Additionally or alternatively to the ninth non-limiting example, the sensing circuitry may be configured for use with a probe having a thermal sensor, and the control circuit is configured to receive data from the sensing circuitry related to temperature sensed by the thermal sensor of the probe and modify one or more parameters of a therapy signal generated by the output stage.

Additionally or alternatively to the ninth non-limiting example, the sensing circuitry may be configured for use with a probe having an optical capability, and the control circuit is configured to receive data from the sensing circuitry related to changes in tissue color observed using the optical capability of the probe and modify one or more parameters of a therapy signal generated by the output stage. In a still further example, the sensing circuitry may comprise an optical source and an optical detector, such that the sensing circuitry can direct an optical signal to the optical capability of the probe and receive an optical signal from the probe indicative of tissue reflectance.

Additionally or alternatively to the ninth non-limiting example, the sensing circuitry may be configured for use with a probe having a transducer, and therefore comprises a driver circuit for driving the probe transducer, and is further adapted to receive a signal from the probe transducer. In a still further example, the driver circuit may be configured to issue ultrasound frequency outputs to an ultrasound transducer in the probe in order to detect changes in fluid density of tissue. In a still further example, the driver circuit may be configured to drive a MEMS based accelerometer, and the sensing circuitry is configured to receive a signal from the MEMS based accelerometer to detect heart sounds. In a still further example, the driver circuit may be configured to drive a MEMS based accelerometer, and the sensing circuitry is configured to receive a signal from the MEMS based accelerometer to detect muscle contractions. In a still further example, the driver circuit may be configured to drive a MEMS based accelerometer, and the sensing circuitry is configured to receive a signal from the MEMS based accelerometer to detect acoustic signals associated with ablation.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 13A-13D show illustrative output and feedback circuits for a signal generator;

DETAILED DESCRIPTION

Figure 1:
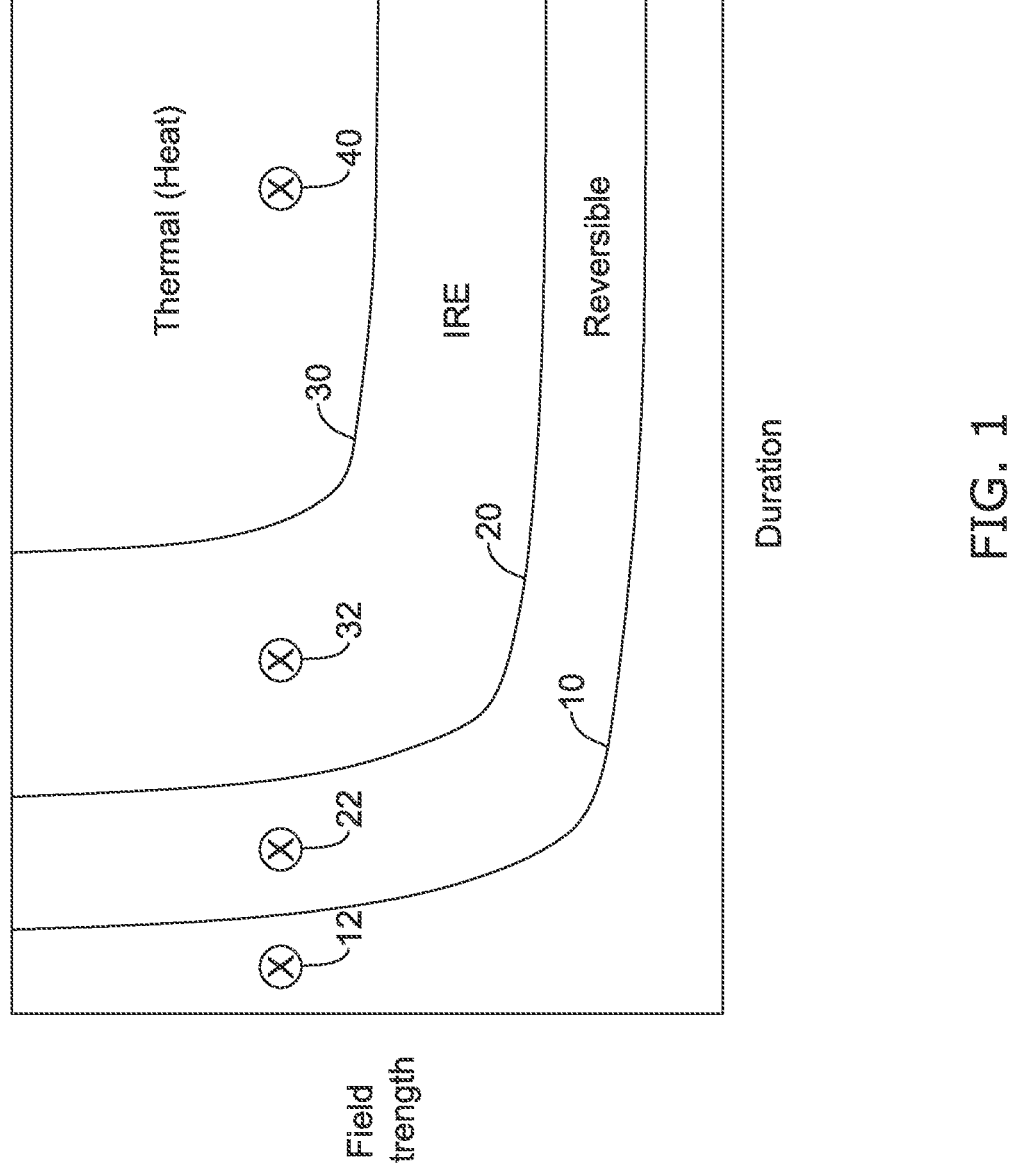
FIG. 1 shows an approximation of different therapy modalities associated with a combination of electrical field strength and pulse duration.

FIG. 1 shows an approximation of different biophysical responses dependent on the amplitude-time relationship of delivered electrical pulses. The thresholds between cellular responses (10, 20, 30) operate generally as a function of applied field strength and pulse duration. Below a first threshold 10, no effect occurs; between the first threshold 10 and a second threshold 20, reversible electroporation occurs. Above the second threshold 20, and below a third threshold 30, primarily irreversible electroporation (IRE) occurs. Above a third threshold 30, the effects begin to be primarily thermal, driven by tissue heating. Thus, for example, at a given field strength and duration there may be no effect (location 12), and extending the duration of the field application can yield reversible electroporation (location 22), irreversible electroporation (location 32), and thermal ablation (location 40).

As described in U.S. Pat. No. 6,010,613, a transmembrane potential in the range of about one volt is needed to cause reversible electroporation, however the relationship between pulse parameters such as timing and duration and the transmembrane potential required for reversible electroporation remains an actively investigated subject. The required field may vary depending on characteristics of the cells to be treated. At a macro level, reversible electroporation requires a voltage in the level of hundreds of volts per centimeter, with irreversible electroporation requiring a still higher voltage. As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067. Generally speaking, a plurality of individual pulses are delivered to obtain such effects across the majority of treated tissue; for example, 2, 4, 8, 16, or more pulses may be delivered. Some embodiments may deliver hundreds of pulses.

The electrical field for electroporation has typically been applied by delivering a series of individual pulses each having a duration in the range of one to hundreds of microseconds. For example, U.S. Pat. No. 8,048,067 describes analysis and experiments performed to illustrate that the area between lines 20 and 30 in FIG. 1 actually exists, and that a non-thermal IRE therapy can be achieved, using in several experiments a series of eight 100 microsecond pulses delivered at 1 second intervals.

The tissue membrane does not return instantaneously from a porated state to rest. As a result, the application of pulses close together in time can have a cumulative effect as described, for example, in U.S. Pat. No. 8,926,606. In addition, a series of pulses can be used to first porate a cell membrane and then move large molecules through generated, reversible pores, as described in US PG Patent App. Pub No. 2007/0025919.

Figures 2, 3, 4:
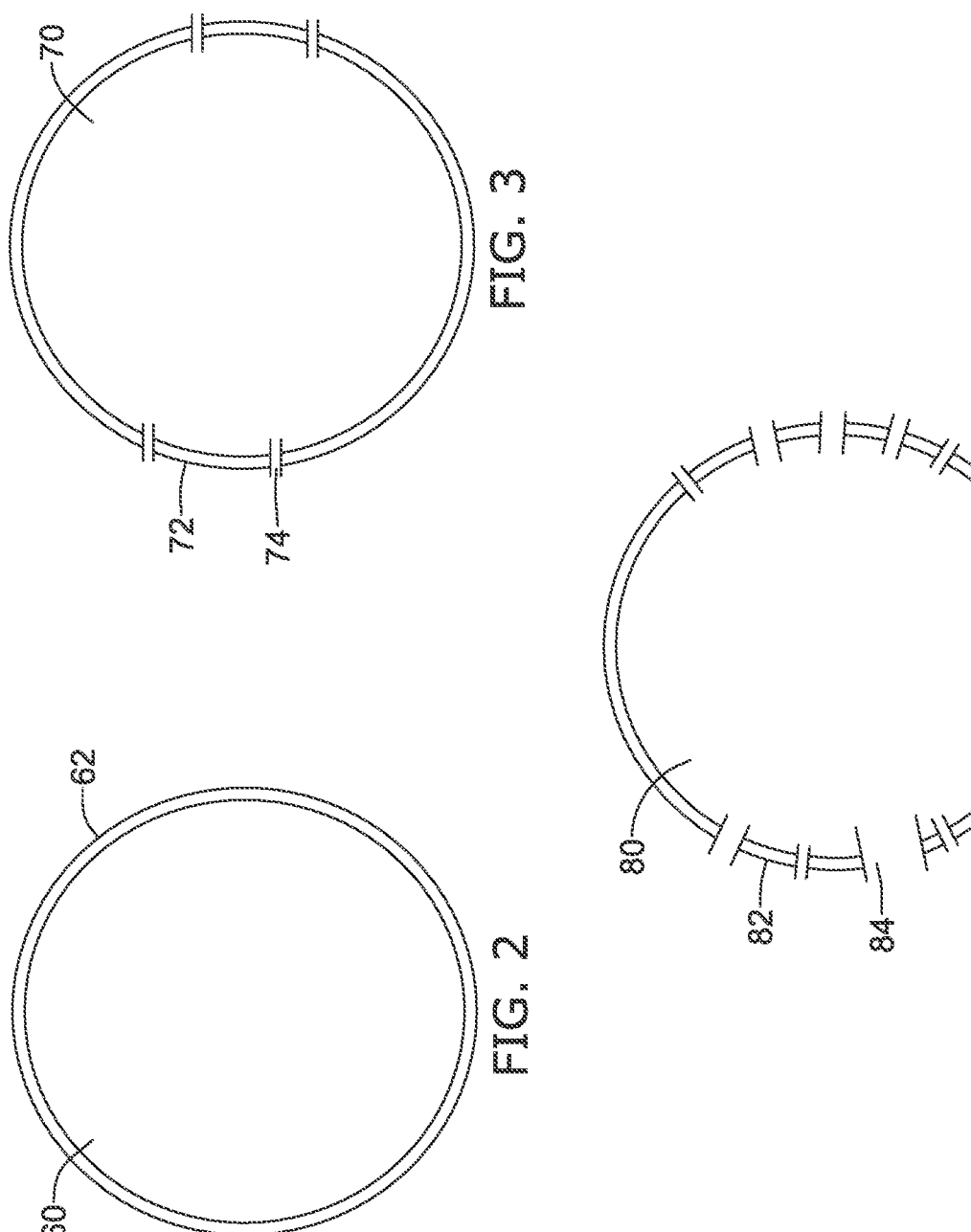
FIGS. 2-4 show various impacts of application of electrical field to a cell.

FIGS. 2-4 show various impacts of application of electrical field to a cell. At electric field strengths below the threshold for reversible electroporation, as shown in FIG. 2, the cell membrane 62 of cell 60 remains intact and no pores occur. As shown in FIG. 3, at a higher electric field strength, above the threshold for reversible electroporation and below the threshold for irreversible electroporation, the membrane 72 of cell 70 develops pores 74. Depending on the characteristics of the applied field and pulse shapes, larger or smaller pores 74 may occur, and the pores developed may last for longer or shorter durations.

As shown in FIG. 4, at a still higher electric field strength, above the threshold for irreversible electroporation, the cell 80 now has a membrane 82 with a number of pores 84, 86. At this higher amplitude or power level, pores 84, 86 may become so large and/or numerous that the cell cannot recover. It may be noted as well that the pores are spatially concentrated on the left and right side of the cell 80 as depicted in FIG. 4, with few or no pores in the region 88 where the cell membrane is parallel to the applied field (assuming here that the field is applied between electrodes disposed to the right and left sides of the cell shown in FIG. 4). This is because the transmembrane potential in region 88 remains low where the field is closer to parallel, rather than orthogonal, to the cell membrane.

Figure 5:
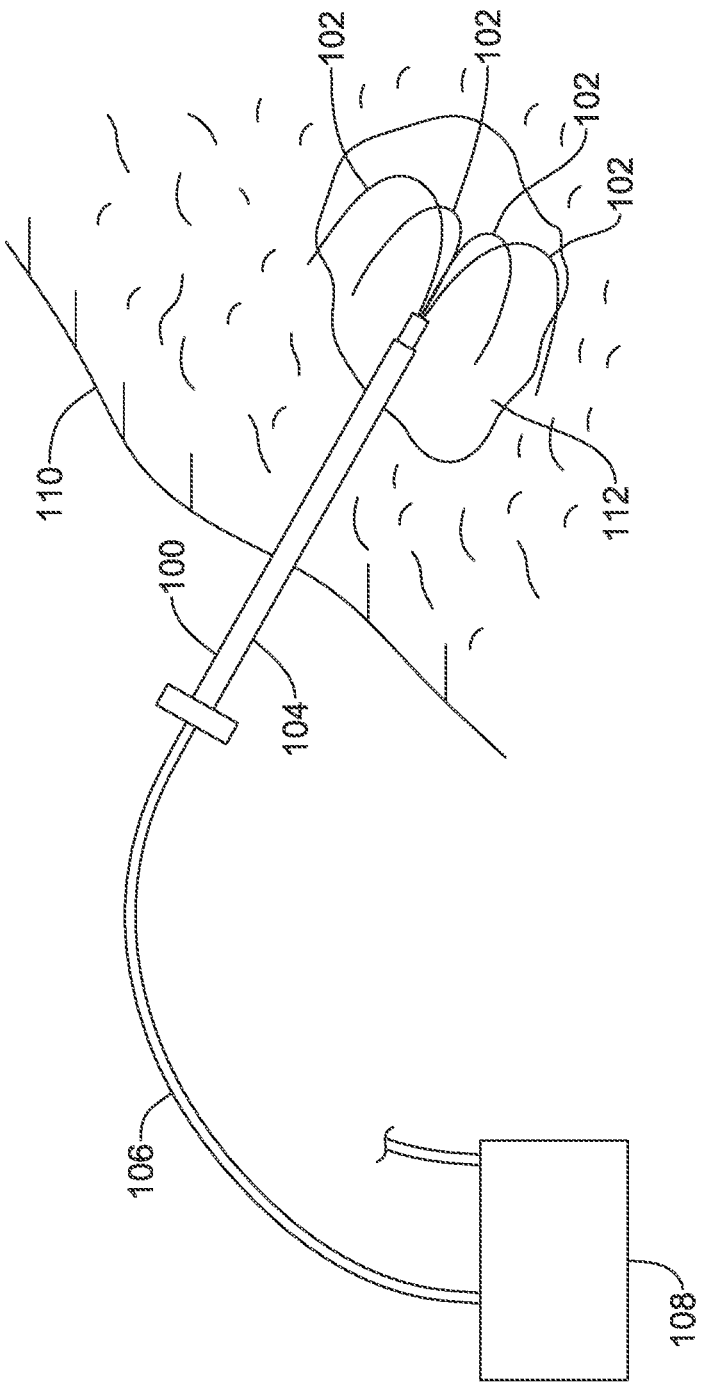
FIG. 5 shows a prior art "Leveen" needle.

FIG. 5 shows a prior art "Leveen" needle. As described in U.S. Pat. No. 5,855,576, the device comprises an insertable portion 100 having a shaft 104 that extends to a plurality of tissue piercing electrodes 102 that can be extended or retracted once a target tissue 112 of a patient 110 is accessed. The proximal end of the apparatus is coupled by an electrical connection 106 to a power supply 108, which can be used to supply RF energy.

Conventionally, the Leveen needle would be used to deliver thermal ablation to the target tissue. For example, as described in the '576 patent, a return electrode in the form of a plate or plates may be provided on the patient's skin, a return electrode could be provided as another tissue piercing electrode, or a return electrode may be provided on the shaft 104 near its distal end, proximal of the tissue piercing electrodes 102.

Enhancements on the original design can be found, for example, in U.S. Pat. No. 6,638,277, which discusses independent actuation of the tissue piercing electrodes 102, both in terms of movement of the electrodes as well as separately electrically activating individual ones of the electrodes. The U.S. Pat. Nos. 5,855,576 and 6,638,277 patents are incorporated herein by reference for showing various probes. U.S. Provisional Patent Application Ser. No. 62/620,873, the disclosure of which is incorporated herein by reference as showing various therapy delivery probes, discloses updates and enhancements on the Leveen needle concept, allowing flexibility in the spacing, size and selection of electrodes.

Figure 6:
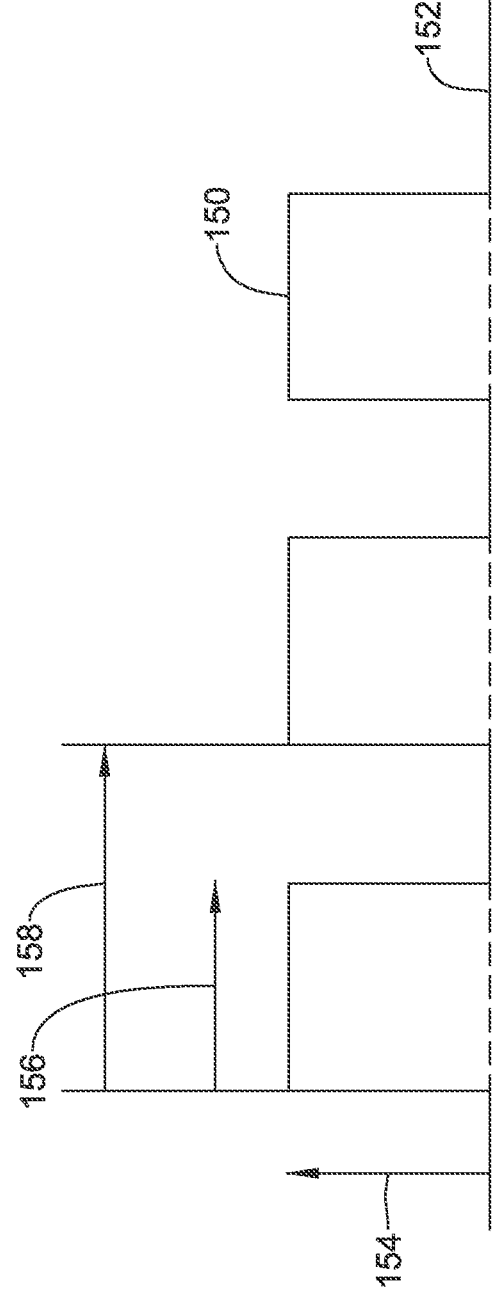
FIGS. 6-8 show various waveform features.
Figure 7:
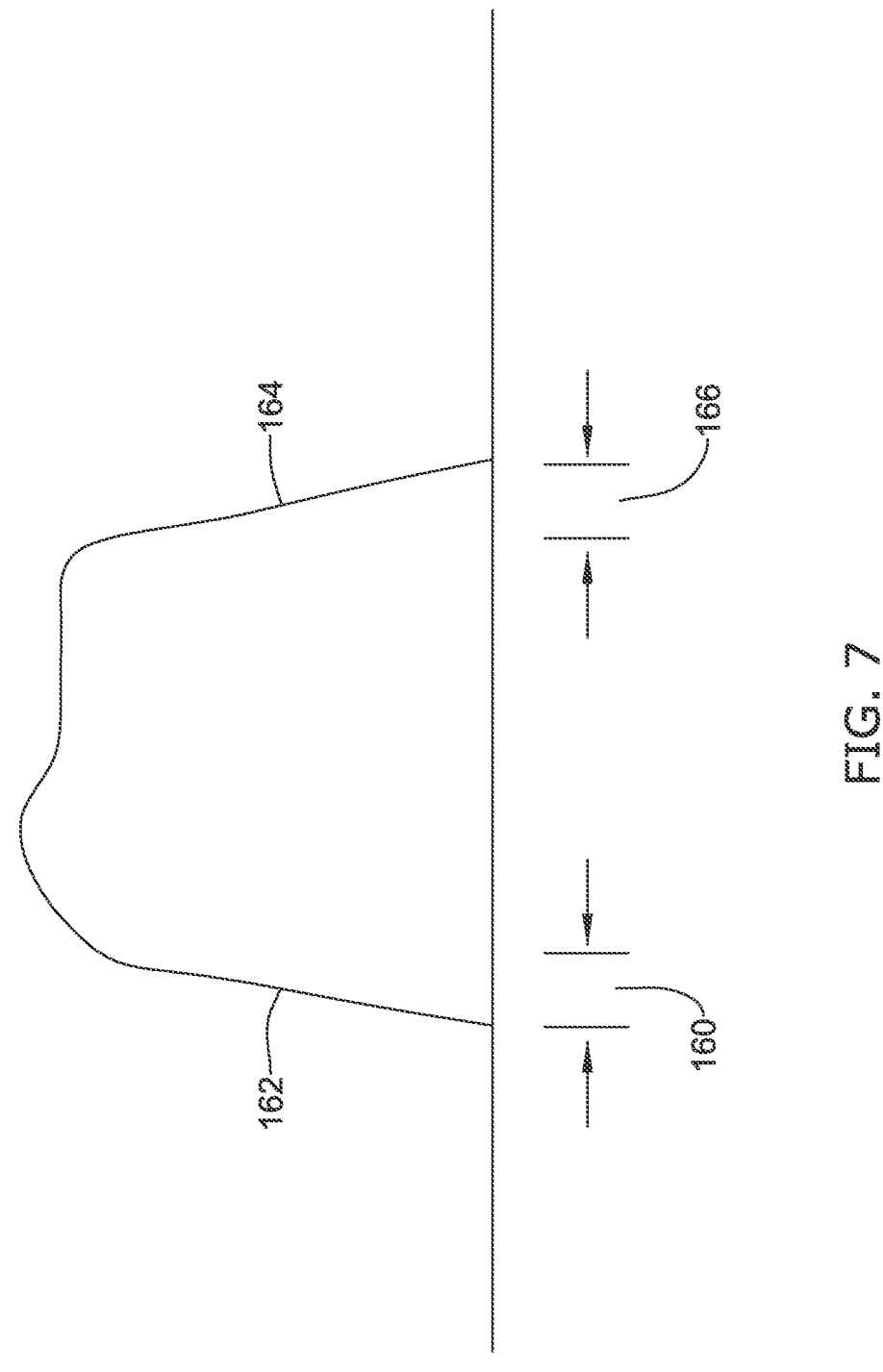
Figure 8:
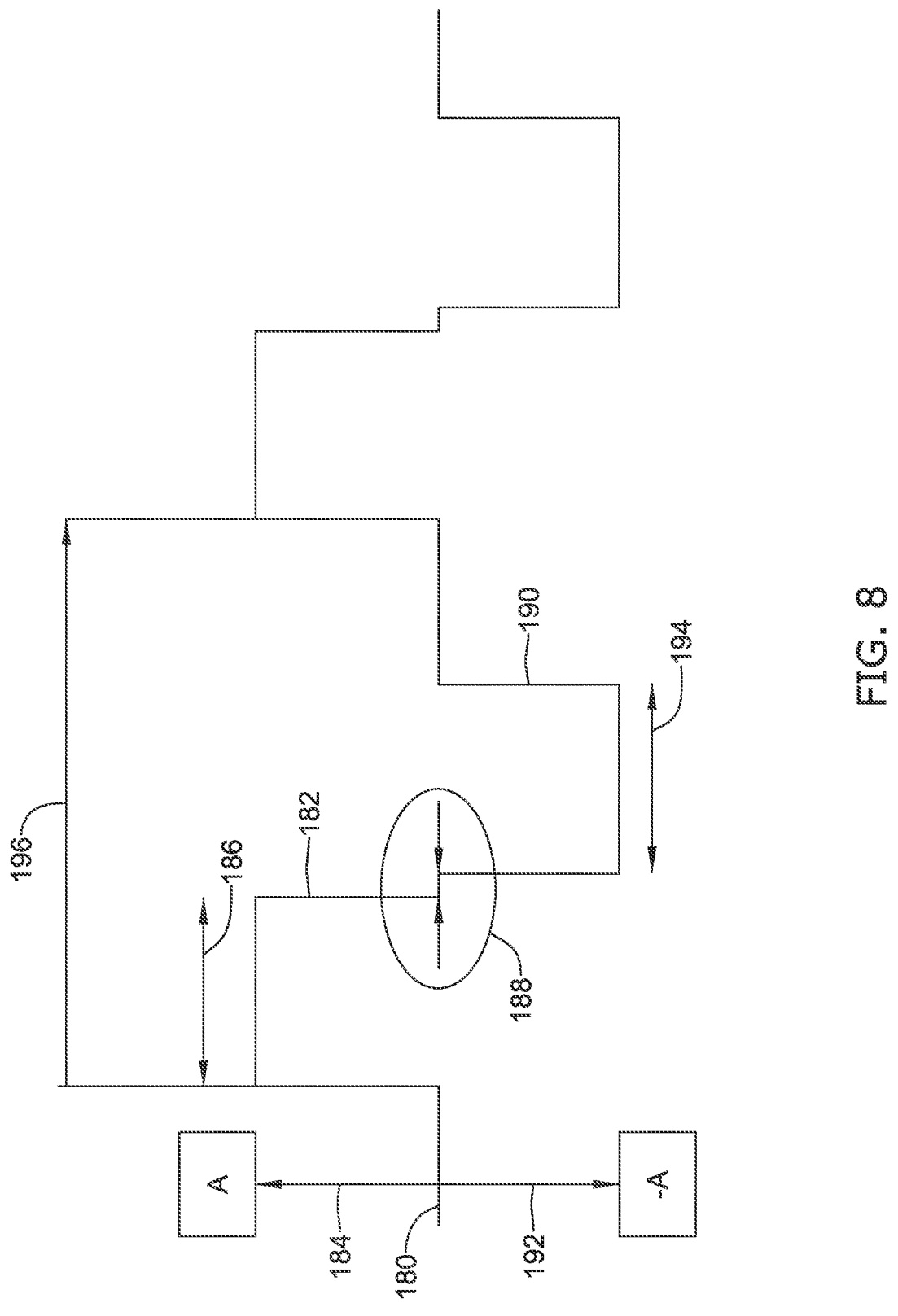

FIGS. 6-8 show various waveform features. Referring to FIG. 6, a monophasic waveform is shown at 150. The waveform 150 is shown relative to a baseline or equipotential 152. An idealized square wave is shown having an amplitude 154, a pulse width 156, and a cycle length 158. The waveform 150 is shown as an ideal square wave, with a vertical upswing from baseline 152 to the designated amplitude 154. When describing such a waveform, the frequency typically refers to the inverse of the cycle length

158. So, for example, if a waveform having a one microsecond pulse width 156 is delivered at two microsecond intervals 158, the "frequency" of the waveform may be described as 500 kHz (the inverse of two microseconds). The waveform 150 may be a current controlled or voltage controlled waveform. Either approach may be used in various examples, as further described below.

In any real application the edges of the generated waveform will be rounded and the upswing from baseline 152 will be more as shown in FIG. 7, where the upward divergence from the baseline, shown at 162, is characterized by a rise time 160. At the end of the output, there is also a non-ideal fall 164 characterized by fall time 166. Real application of the waveform will also include some variation in the peak amplitude, as shown, which may include for example overshoot of the amplitude if the signal output is underdamped, or rounding off of the edges for a critically damped or overdamped signal.

In some examples, one or more of the rise or fall time 160, 166 can be manipulated. In an illustrative example, the output circuitry of a system may include selectable elements, such as resistors, inductors or the like, that can slow the rise time if switched into the circuit. For example, the current through an inductor cannot be instantaneously changed, so switching an inductive element into an output circuit can slow the rise time as the inductor begins to allow current to flow.

Rise and fall time may be manipulated in several different ways. For example, the process settings may be selected to modify the peak voltage target; a higher target can yield a faster rise time as various components respond in exponential fashion to being turned on or switched into an output circuit. By monitoring the output, the system can artificially increase a peak voltage target to reduce rise time, and once the true peak voltage is met, the system may switch voltage sources or use an output regulation (such as by using a rectifier or by redirecting output current through a separate discharge path) to cap the voltage output. In another example, component selection may be used, such as by having a plurality of different HV switches available and selectable to the system, with different HV switch types having different rise and fall times. For example, if three output switches are available, each with a different rise/fall characteristic, the system may respond to a user input requesting longer or shorter rise/fall time by selecting an appropriate output switch for use during a particular therapy output session. High pass or low pass filtering may be switched into the output circuit as well to control slew rate, or may be switched into the control signal circuit; a slow turn-on of an output transistor for example can cause slower rise time for the transistor itself and conversely fast turn-on of the output transistor can speed the rise time. In another example, a digital to analog converter may be used as an output circuit, allowing digitized control of rise or fall time. In still a further example, control signals to the output switches can be generated by a digital to analog converter, thus manipulating the on/off signal to the output circuitry itself. In still a further example, using a capacitor stack output as shown in several examples herein, a fast rise time may be effected by using a single switched output from the top (or desired target level) of the capacitor stack, while a slow rise time may be effected by sequentially turning on an output using less than all of the capacitor stack and then subsequently adding more of the capacitor stack to the output; appropriately placed diodes in the output circuitry will prevent back-current or shorting of the newly added portions of the capacitor stack during such a maneuver.

FIG. 8 shows further details, this time for a biphasic signal. Here, the waveform is shown at 180, with a first, positive pulse at 182 quickly followed by a negative pulse at 190. The positive pulse 182 has an amplitude 184, and the negative pulse 190 has an amplitude 192 which is usually equal in voltage to, but of opposite polarity than, the positive pulse. The positive pulse 182 has a pulse width 186, and the negative pulse 190 has a pulse width 194; again, typically the two pulse widths 186, 194 would be equal to one another. For a signal as shown, the cycle length can be determined as shown at 196, from the start of the positive pulse 182 to the initiation of a subsequent cycle; again, frequency is the inverse of the cycle length.

In a typical application or use of biphasic signals, the aim is, in part, to achieve charge balancing at the end of each cycle. For that reason, the pulse widths of the two phases are kept equal, and the amplitudes are also equal though of opposite polarity. Whether using a voltage controlled or current controlled system, charge balance can be reasonably maintained by controlling just the pulse width and amplitude. For example, in a voltage controlled system, the current flow will be more or less constant within a cycle, assuming the cycle length 196 is fairly short. That is, while it is known that during ablation procedures the tissue impedance changes as cells are destroyed, expelling cellular media which generally reduces impedance, the impedance does not change so quickly that charge balancing of a simple biphasic waveform, even one that does not control current, would become an issue. In some examples below, however, the delivered energy is not a "simple biphasic" waveform insofar as the period between two phases is extended to a duration that is more than half the duration of either phase, for example, in which case it becomes more likely impedance changes can result in a charge imbalance that triggers or risks muscle stimulation.

An interphase period 188 represents a time period spent at baseline between the positive and negative pulses, and is ordinarily minimized in accordance with the physical constraints of the underlying circuitry. Thus, for example, if a first switch must turn off to end the positive pulse 182, and a second switch is used to initiate the negative pulse 190, assuming digital control, the system may allow a few digital clock cycles to expire after turning off the first switch before turning on the second switch, to avoid any possible internal shorting. Faster switches can reduce the interphase time, and much engineering effort has gone into reducing this time period 188.

For example, a very short interphase period 188 can be achieved using a design as shown in U.S. Pat. No. 10,154, 869. In the U.S. Pat. No. 10,154,869 Patent, an inductor is placed in parallel with the output load. A power source is applied to the load and inductor during an initial phase of therapy delivery. Opening a switch between the power source and the load/inductor causes a near immediate reversal of current through the load as the inductor draws current from the load after the power source is disconnected.

The background to be gathered from FIGS. 6-8 is that of typical usage. In several embodiments described further below, monophasic pulses are used to achieve biphasic results with respect to charge balancing that prevents muscle stimulation. It should be noted that within the examples herein, the term "without causing muscle stimulation" allows for some muscle stimulation, but only an amount tolerable within the relevant intervention and/or surgical domain. For example, the stimulation that occurs is not so much that the patient is made uncomfortable. In another example, the stimulation that occurs is small enough that surgery to ablate tissue is not subject to interference due to stimulated patient movement. In another example, the muscle stimulation that occurs is insignificant to the surgery and allows surgery to be performed without requiring administration of a paralytic. In some examples, the stimulation that occurs does not affect probe placement and securement, or is small enough that migration of the probe does not occur. As used herein, a meaningful charge imbalance for ablation therapy purposes is one that triggers, either within a single cycle or over a plurality of cycles, muscle stimulation that affects a surgery. In several embodiments the aim is to provide enhanced therapy—mimicking monophasic therapy—while avoiding and/or preventing meaningful charge imbalance.

Figure 9:
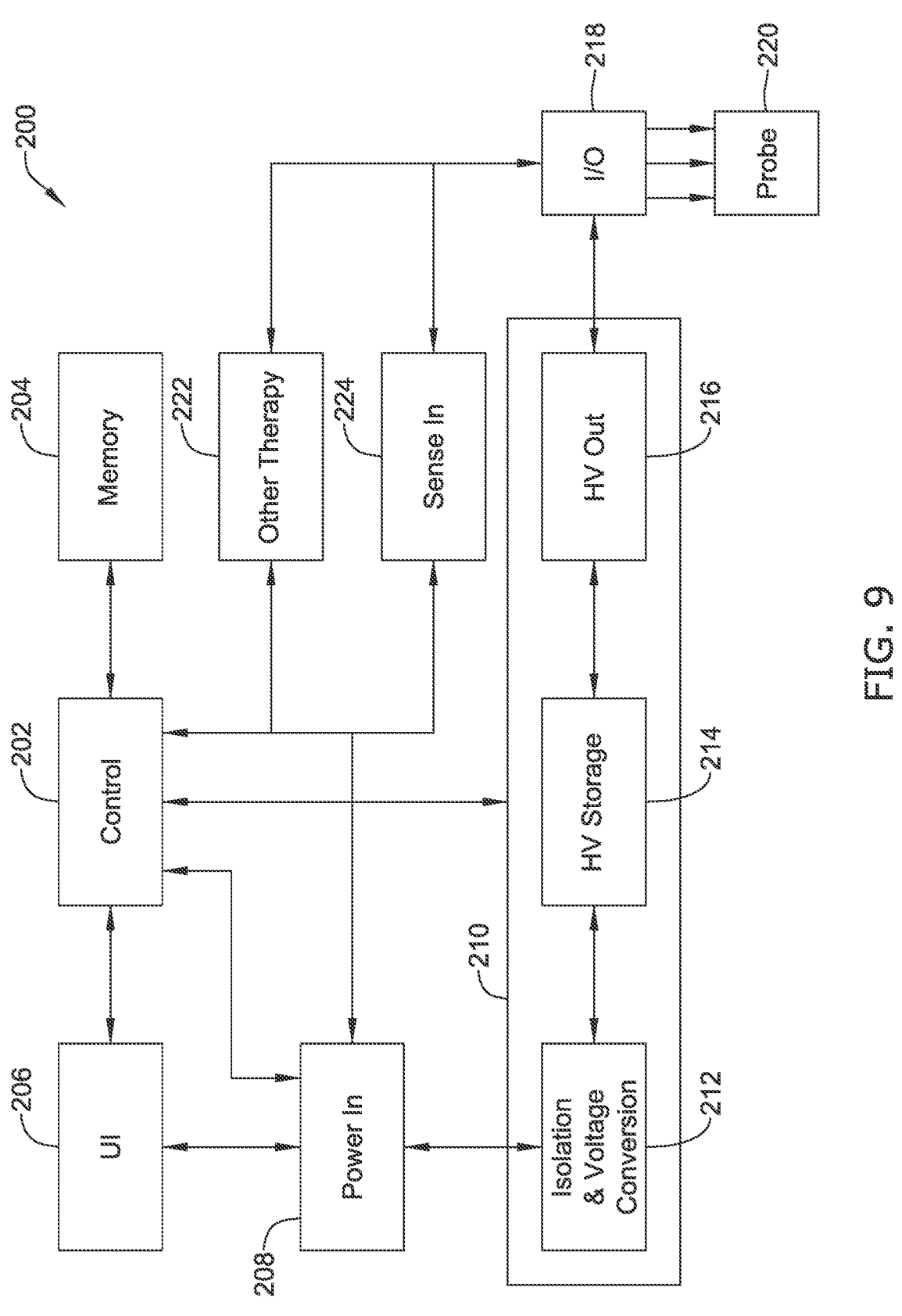
FIG. 9 shows a signal generator in block form.

FIG. 9 shows a signal generator in block form. A signal generator 200 may be a self-contained unit, or it may comprise several discrete components coupled together with wires and/or wireless connections. A control block is shown at 202 and may comprise a plurality of logic circuits in the form of a state machine, a microcontroller, a microprocessor, or even an off the shelf computing unit such as a laptop or desktop computer, as desired, and may further include various associated analog and/or digital logic, application specific integrated circuits (ASIC), dedicated hardware circuits, etc. For example, the output energy of the system may be delivered at much higher amplitudes than the operational logic uses (i.e., hundreds or thousands of volts for the outputs, with logic and processing performed at amplitudes generally under ten or even five volts). Thus there may be included isolation circuitry, voltage dividers or the like to reduce the systems operating voltages to levels more readily handled by the control circuitry. Dedicated circuits, such as ASIC circuits, may be used for processing high speed operations or to convert measured voltages or currents to digital outputs by including, for example, dedicated analog-to-digital conversion circuits, dedicating sampling circuits to samples voltages or currents, etc. In addition, optical isolator elements are often used in the art to allow low voltage control over high voltage circuitry, for example.

A memory 204, which may or may not be separate from the control block 202, is included to store executable instruction sets for operation as well as keeping a log of activity of the system and any sensor outputs received during therapy. The memory 204 may be a volatile or non-volatile memory, and may include optical or digital media, a Flash drive, a hard drive, ROM, RAM, etc. A UI or user interface 206, which may also be integrated with the control block (such as when using a laptop for control 202, which would include each of memory 204 and a UI 206). The UI 206 may include a mouse, keyboard, screen touchscreen, microphone, speakers, etc. as desired.

Power in 208 may include a battery or batteries, and/or an electrical coupling to plug into a wall socket to receive line power. A therapy block is shown at 210 and includes several stages. An isolation and voltage conversion circuit is shown at 212 and may include, for example, one or more transformers or other step-up converters (such as a capacitive step-up conversion circuit) to take a battery or line voltage and increase to a high voltage output that is stored in HV storage 214. The HV storage 214 may include batteries, inductors or other circuit elements, but will typically be a capacitive storage block such as a stack of capacitors. HV storage 214 may be helpful to take the HV signal from block 212 and smooth it out over time to provide a more stable high voltage output that is then delivered by an HV output circuit 216. Also, the HV storage 214 may enable a lower power voltage input to generate very high power outputs by storing energy over a longer period of time to be delivered in short bursts.

The HV output circuit 216 may include a number of switches and other elements, including for example, high voltage switches such as silicon controlled rectifiers, high power Mosfets, and other elements, allowing selective outputting of the high voltage signal to an IO block shown at 218. In some examples, the HV output circuit may be driven using one or more optical isolators or other isolation circuitry or circuit elements to allow isolation of lower power logic and control circuitry from the higher power/amplitude circuitry. The IO block 218 may provide a number of sockets to receive plugs from one or more delivery probes 220, as well as one or more outputs for one or more indifferent electrodes to be placed on the body of a patient, serving as return electrodes or simply grounding the patient and system. For illustrative purposes the drawings show individual outputs as if there are separate plugs for each but embodiments herein also include compound plugs and/or ports that facilitate plural electrical connections via a single mechanical coupling.

In some alternative approaches to the therapy block 210, rather than HV Out 216 using sets of switches to directly output a signal from HV storage, a resonant circuit may be powered by the HV signal, with outputs of the resonant circuit used for therapy delivery by selectively switching the output of the resonant circuit. A topology that uses a set of four switches in an "H-bridge" to drive an RF circuit is shown, for example, in U.S. Pat. No. 10,105,172. In some embodiments, control over the individual pulses is achieved in the present invention by omitting the driven RF circuit and relying on a form of extended H-bridge circuit, as shown below in additional figures and description. Additional details that can be used in some embodiments are shown in additional figures below. Certain user interface features are also highlighted below in additional figures and description.

One or more sensing circuits 224 may be included to provide feedback to the control block 202. For example, the sensing circuits may measure voltage at the output nodes to the probe 220, or may measure current going to the output nodes that couple to the probe 220, allowing tissue characteristics to be monitored. For example, voltage measuring circuits are well known in the art, including, for example, direct-conversion, successive approximation, ramp-compare, Wilkinson, integrating, Delta-encoded, pipelined, sigma-delta, and/or time-interleaved ADC, any of which may be used as suited to the application. Current measuring circuitry may use, for example, trace resistance sensing, a current sensor based on Faraday's Law such as a current transformer or Rogowski coil, or the use of magnetic field sensors (Hall effect, Flux gate, and/or a magneto-resistive current sensor) electrically or magnetically coupled to one or more transmission lines.

In another example, the probe 220 may include a sensor, such as a temperature sensor, a force sensor, or a chemical or pH sensor, any of which can be used to monitor tissue characteristics during therapy delivery. For example, a temperature sensor may be used to manage a non-thermal therapy such as electroporation by observing whether the temperature in a region is raising above a threshold temperature or showing an increasing trend, in which case one or more elements of power output may be reduced to ensure that the desired therapy type is dominant. If the probe contains such items, the sensing circuits 224 may include any suitable amplifier, filter or the like to allow the sensed signal to be conditioned for use by the control block 202.

Sensing circuits 224 may include a cardiac rhythm sensor that is adapted for use with one or more electrodes (such as surface electrodes placed on the patient's chest) to capture cardiac rhythms and identify physiological windows for therapy delivery. A cardiac signal for purposes of identifying a physiological window for therapy may be received instead from an in-clinic ECG monitor, an implantable medical device such as a subcutaneous cardiac monitor, or a pacemaker or defibrillator, or from a variety of wearable products that sense cardiac rhythms. Rather than using the ECG, heart sounds, or pulse oximetry may be used to identify cardiac cycles and select therapy windows.

In addition, a probe as shown in FIG. 5 may include one or more imaging apparatuses, such as a lens coupled to a fiber optic cable to capture images at or near the probe. For example, a combination lens and fiber optic cable may be provided on one or more of the tissue piercing electrodes, at a distal end thereof or proximal thereto. The fiber optic cable may have a single strand to simply receive optical images. In some examples a fiber optic cable may have more than one strand to allow for two "channels", using one to illuminate the vicinity of the lens, and the other to receive reflected light, or a splitter may be used at the proximal end to allow pulsed light output to be provided into a single strand and reflected light to be directed to a feedback channel, which is then routed to an optical sensor. As ambient or reflected light changes, one can observe changes in tissue color indicating blood perfusion ongoing or ceasing, or indicating changes in the local tissue. The sensing circuitry 224, in some illustrative examples, may be adapted for such use by having an optical output generator (an LED, VCSEL, or other suitable light generator) and an optical receiver. A lens may or may not be needed; it may be sufficient to provide a fiber optic strand with a cleaved end placed in contact with tissue that allows light to exit and enter.

In another example, one or more transducers may be placed on a probe as shown in FIG. 5 to serve a plurality of purposes. An accelerometer may be used both to sense muscle motion, as well as to sense other vibrations such as acoustics. Either by issuing an output acoustic ("ping") and receiving feedback, or simply "listening", the transducer may be used to determine whether any sounds are taking place indicative of physical changes in the region of the therapy electrodes. For example, if arcing occurs between two electrodes this can generate thermal energy that can cause vaporization, which may generate acoustic waves that can be sensed. An ultrasound transducer may be provided as well, allowing the use of ultrasound to measure changes in tissue fluid density. For each such transducer, the sensing circuitry 224 may comprise a driver circuit, such as an operational amplifier, to provide energy to the transducer via one or more electrical connections in the I/O circuitry 218 and probe 220. As noted above, heart sounds may be obtained for use in timing therapy delivery; such a transducer may also be used to obtain heart sounds. For observing acoustic energy and/or muscle motion, a one, two or three axis micro-electro-mechanical system (MEMS) sensor may be used. Such a transducer typically has a vibrating element that changes an electrical parameter as motion is observed. Such a transducer can be referred to generally as an accelerometer, and may be integrated for example into a probe adapted for ablation therapy delivery. Filtering the output to different frequency ranges in one or more channels may be useful to separately observe patient motion, heart sounds, and/or thermal ablation sourced sounds. Voltage and/or current sensing circuitry already described for block 224 may be used to receive, sample, and/or condition signals returned from the transducer, as needed.

Optionally, "other therapy" block 222 may be included. "Other" therapy may include, for example, the delivery of a chemical or biological agent to provide additional therapy, to enhance therapy being delivered, or to trigger immune response to facilitate the body healing itself after ablation. Such other therapy 222 may comprise a reservoir (which may be refillable) of material to be delivered to a patient via, for example, a syringe or catheter or through a probe. An "other therapy" 222 may include introducing a substance that enhances, augments, is synergistic with, or independently adds to the ablation effects of therapy delivered electrically. For example, a substance may be injected to modify or enhance electric field effects, as disclosed in U.S. patent application Ser. No. 16/188,343, titled IRREVERSIBLE ELECTROPORATION THROUGH A COMBINATION OF SUBSTANCE INJECTION AND ELECTRICAL FIELD APPLICATION, the disclosure of which is incorporated herein by reference.

In some examples, a cryotherapy may be integrated into the system to allow tissue cooling before, during or after electrical ablation, prompting immune response if desired. Cryotherapy may be delivered using, for example, a balloon on a therapy probe 220 or provided separately with a nozzle in the balloon coupled to a pressurized fluid source, such as nitrous oxide; the pressurized fluid when expelled through the nozzle will expand or go through a phase change from liquid to gas, which causes localized cooling, as disclosed for example in U.S. Pat. No. 6,428,534. In another example, a fluid (gas or liquid) may be externally cooled and introduced via a catheter for cryogenic purposes, or, in the alternative, externally heated and introduced via a catheter for heat ablation purposes.

In still other examples, other therapy 222 may include delivery of energy such as mechanical energy (ultrasound, for example) or optical energy using, for example, a laser source (such as a vertical cavity surface emitting laser, or other laser source) coupled to an optical fiber that extends through a probe to allow laser energy to be delivered to targeted tissue. In some examples, a secondary or "other" therapy may be used, as noted, to trigger the immune response even if it is not used as a primary approach for destroying targeted tissue. The modality of "other therapy" 222 may overlap with some of the features of the sensing circuitry, and so the same circuit elements may be considered as part of each block. For example, a laser therapy output may be provided via the I/O, as well as a coupling for optical interrogation of tissue characteristics via an associated probe. Each may use the same or different optical tranducers. In one example, a VCSEL is provided for use by "other therapy" and is reused as needed to provide a lower energy output for optical tissue interrogation by the sensing circuitry 224.

For safety purposes, current sensors on the output circuitry may be used to limit shorting or overcurrent conditions. For example, the Sense In block 224 may detect overcurrent at the I/O 218 and signal the control circuitry 202, which may in return cut of power to the voltage conversion circuit 212 and/or disable HV Out 216 to turn off the output circuit (opening a switch, for example) in response to sensed overcurrent. In some embodiments, the Sense In block 224 may capture peak current during any therapy output in order to sense for transient events or trends that pose a risk of component damage. Meanwhile, sensed current for other purposes, such as to determine impedance, may be the peak sensed current during stimulus output or may be defined as an average current during the stimulus and more specifically during a particular one of the output phases or plurality of output phases. If taking average current, the sense circuitry may determine begin and end points in time, relative to a system clock, so that the control circuitry can align sensed current with phases and other characteristics of output stimuli.

Additionally or alternatively, the output circuitry in the I/O block 218 and/or HV out 216 may include a fuse, if desired. Additional safety features may include the provision of a temperature sensor associated with the voltage conversion circuitry 212, HV storage 214, HV out 216 and/or I/O 218; a temperature that is too high may cause the system to shut down. In other examples, one or more temperature sensors may be used to prevent operation if the signal generator 200 is too cold, as may happen if it is stored or transported in a vehicle in cold weather prior to use. One or more temperature sensors may be provided on the probe to be used with the system to enable or disable operation. For example, a too cold temperature (for example, well below body temperature) may indicate that the probe 220 is not yet applied to tissue, and the control circuit 202 may prevent stimulus delivery or may provide a warning on the UI 206 to the user that the probe 220 is not showing body temperature conditions. A too hot temperature at probe 220 may signal thermal damage that is occurring in a manner that will be poorly controlled, as may happen if two contacts of the probe are too close together or shorted; again, the control circuitry 202 may be configured to turn off or modulate intensity. A temperature sensor on the probe 220 may be used for active feedback as well, as the control circuit 202 may modulate therapy amplitude and/or pulse width to attain a desired temperature range during therapy. For example, the temperature may be maintained in a predetermined range for non-thermal effects or for thermal effects, such as by keeping temperature above or below a temperature in the range of 50 to 60 degrees centigrade.

Figure 10:
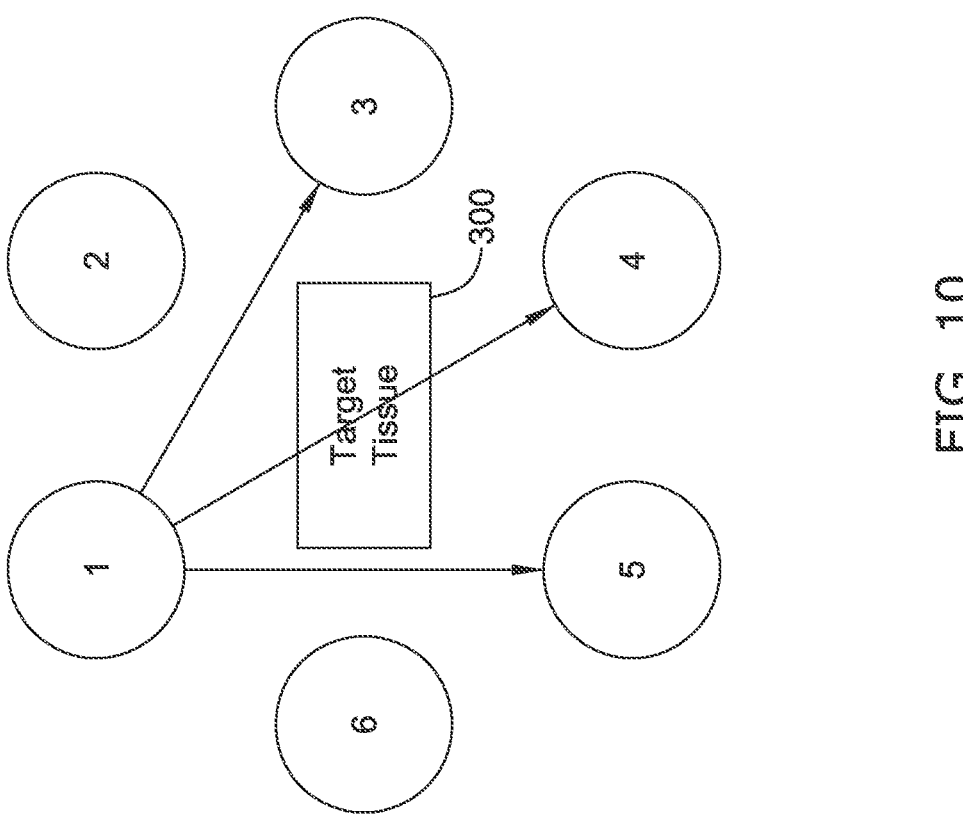
FIG. 10 shows a target tissue with electrodes thereabout.

FIG. 10 shows a target tissue with electrodes thereabout. As shown in FIG. 10, a target tissue 300 may be surrounded by a plurality of electrodes 1-6. A probe as shown above in FIG. 5 may be readily used to place several electrodes around a target tissue 300, with the individual electrodes 1-6 piercing and advancing through tissue around the target. In conventional biphasic application, the electrodes may be used in pairs or groups or as a complete group relative to a remote return electrode, with a positive phase signal immediately followed by a negative phase signal of generally equal but opposite voltage or current. In contrast to such uses, the present invention instead uses a spatial multiplexing of the therapy outputs to deliver therapy with the effectiveness of monophasic outputs while taking advantage of biphasic therapy's reduced side effects (particularly, muscle stimulus). To do so, in one example, electrodes may be used to deliver monophasic therapy in a round-robin type of fashion as follows:

| Step | Cathode | Anode |
|---|---|---|
| A | 1 | 4 |
| B | 2 | 5 |
| C | 3 | 6 |
| D | 4 | 1 |
| E | 5 | 2 |
| F | 6 | 3 |

For this example, each of the outputs may be a monophasic waveform. Pulse width and amplitude during the sequence may be kept constant or may vary, if desired. In an example, the pulse width is in the range of 0.1 to 10 microseconds for each pulse. The amplitude may be determined on a voltage or current basis, or may be determined using, for example, a visualization or distance estimation to provide an output in volts per centimeter. For example, an output amplitude may be selected to account for such a distance while exceeding the threshold for IRE for the target tissue 300. In an example, electrodes 1 and 4 may be estimated to be 2 centimeters apart, a calculation that could be made using radiography or other visualization, or which could be determined by assuming an impedance per unit distance for the tissue in region of probe deployment, measuring the impedance between electrodes 1 and 4, and then calculating the distance.

Therapy may be delivered, referring to the above chart, sequentially in any order—that is, A-B-C-D-E-F may be the order. In some examples, the sequence A-D may be avoided, as that would essentially be a biphasic output in form even if not in name and therefore may not be as effective as a monophasic output. In some examples, to avoid back-to-back or immediate reversal of the electrode pairing, a rule may be set requiring at least one electrode be different for any given pulse delivery, from the immediately preceding pulse delivery.

The completed sequence, in some examples, is delivered as a pulse train that is completed within time period(s) that meet each of two rules:

Charge balance rule: the pulse train is completed thereby providing charge balance or an approximation of charge balance within:

A time period that is less than the time constant of surrounding tissue, which can depend on factors such as tissue type and water content. The time constant of surrounding tissue reflects the complex impedance of the tissue and cells in the electrical field. For example, the time constant of the tissue between two electrodes would be determined by the complex impedance thereof; in a simplified model the time constant would be the capacitance multiplied by the resistance of the tissue, including cells, within the electrical field that would be generated between two electrodes. Cells or tissue which is already polarized may have a greater or lesser effective time constant.

A time period of less than about one millisecond

A maximum time period tolerable for the patient, as determined by testing the patient. For example, to test a patient, a therapy output may include first and second portions separated by a period of time, and the period separating the first and second portions can be extended until muscle contraction is observed, until the patient reports feeling a contraction or tension, or until discomfort is indicated by the patient, wherein the first portion of the therapy is a first monophasic pulse or pulses that impart a charge imbalance, and the second portion of the therapy is configured to remove the charge imbalance. For example, a biphasic output may be separated into two portions by controlling and expanding the interphase period (FIG. 8, 188) to a multiple of the individual pulse widths—such as using 5 microsecond pulses separated by tens or hundreds of microseconds, or even more, out to several milliseconds, as tolerated by the patient and while still staying within the therapy completion rule noted below.

Therapy completion rule: the pulse train is to be delivered
within a physiological window determined by obser-
vation of a non-therapy factor, such as the cardiac
rhythm of the patient.

Regarding the therapy completion rule, using the heart as
the driver, the cardiac rhythm contains various components
known by convention as the R-wave, QRS complex,
P-wave, and T-wave. Stimulus for ablation purposes ought
not interfere with the cardiac rhythm, and the heart may be
less susceptible to electrical signal interference in an interval
between the R-wave peak (or end of the QRS complex) and
the T-wave. Sometimes this interval can be called the S-T
interval (the S-wave ends the QRS complex); the S-T
interval for a given patient is likely to last tens of millisec-
onds and may range from 5 to 100 milliseconds. Approxi-
mately 60 milliseconds is typical for a healthy individual,
though it is noted that the therapies discussed herein are not
necessarily for healthy or typical people and, therefore, the
S-T interval may not be "typical". In any event, in some
examples, therapy is started and completed within the S-T
interval window. A cardiac signal useful for identifying the
S-T interval, or other physiologically useful window, may be
obtained from a separate device (external or implantable) or
may be sensed by a therapy generator having inputs for
receiving cardiac signals from electrodes placed in or on the
patient. Other sources may be the drivers; for example,
detecting diaphragm movements may be useful as well, to
time delivery of therapy for when the patient has inhaled, or
exhaled.

In other examples, one, the other, or both of these timing
rules may be omitted. In some examples, the windows may
be approximated, such as by setting a rule that a pulse train
must return to a balanced charge state in less than one
millisecond, or 800 microseconds, or 500 microseconds.

In another example, plural electrodes can be ganged
together as cathode:

| Step | Cathode(s) | Anode(s) |
|---|---|---|
| A | 1, 2, 3 | 5 |
| B | 2, 3, 4 | 6 |
| C | 3, 4, 5 | 1 |
| D | 4, 5, 6 | 2 |
| E | 5, 6, 1 | 3 |
| F | 6, 1, 2 | 4 |

In still another example, plural electrodes may be ganged
together as the anode:

| Step | Cathode(s) | Anode(s) |
|---|---|---|
| A | 1 | 3, 4, 5 |
| B | 2 | 4, 5, 6 |
| C | 3 | 5, 6, 1 |
| D | 4 | 6, 1, 2 |
| E | 5 | 1, 2, 3 |
| F | 6 | 2, 3, 4 |

Both anodes and cathodes can be ganged:

| Step | Cathode(s) | Anode(s) |
|---|---|---|
| A | 1, 2 | 4, 5 |
| B | 2, 3 | 5, 6 |
| C | 3, 4 | 6, 1 |
| D | 4, 5 | 1, 2 |

18

-continued

| Step | Cathode(s) | Anode(s) |
|---|---|---|
| E | 5, 6 | 2, 3 |
| F | 6, 1 | 3, 4 |

Various such pairings may be used. As noted then, the
therapy can be delivered according to a rule set. An appa-
ratus for delivering therapy may incorporate such a rule set
into stored instruction sets or hardwiring, as desired.

In light of the above, an illustrative example takes the
form of a method of therapy delivery comprising delivering
a plurality of monophasic outputs between selected pairs or
groupings of electrodes in a pulse train Further the therapy
delivery and pulse train may be delivered using a first rule
that calls for each successive pulse in the pulse train to use
at least one different electrode (whether by omitting a
previously used electrode, adding an electrode, or swapping
one or more electrodes for one or more other electrodes)
than an immediately preceding pulse. A second rule calls for
the pulse train to be delivered within a preset period of time,
such as less than the time constant of surrounding tissue or
less than one millisecond. A third rule calls for the pulse train
to be delivered within a specified physiological window,
where the physiological window corresponds to time within
the cardiac cycle when the heart is refractory to or at least
relatively less susceptible to electrical interference. Another
illustrative example may take the form of a signal generator
as shown above in FIG. 9 which stores in executable form
or which is otherwise configured to incorporate the first,
second and third rules. For each of these illustrative
examples, output therapy pulses may be, for example, in the
range of about 0.1 to 10 microseconds per pulse, with a pulse
train of any suitable length, such as about 4 to about 100
pulses, and the pulse train may be repeated.

In some examples, as therapy is delivered using the
various electrodes, output current in or out of each electrode
may be tracked. At the end of a pulse train, or series of pulse
trains, the sum of currents through each electrode may be
determined, and one or more corrective outputs generated as
by delivering a current or voltage of a predetermined amount
that is likely to offset any built-up charge at any one
electrode interface. Various illustrative examples may
include a combination of monitoring charge delivered and
then providing a "corrective" pulse to negate any built up
charge on any one or more of the electrode surfaces. A
corrective pulse may be useful in particular when a voltage
controlled output, rather than a current controlled output, is
used. Additional examples that build off of, or show alter-
natives to, FIG. 10, can be found in U.S. Provisional Patent
Application 62/819,135, filed Mar. 15, 2019, titled SPA-
TIALLY MULTIPLEXED WAVEFORM FOR SELEC-
TIVE CELL ABLATION, the disclosure of which is incor-
porated herein by reference.

Figure 11:
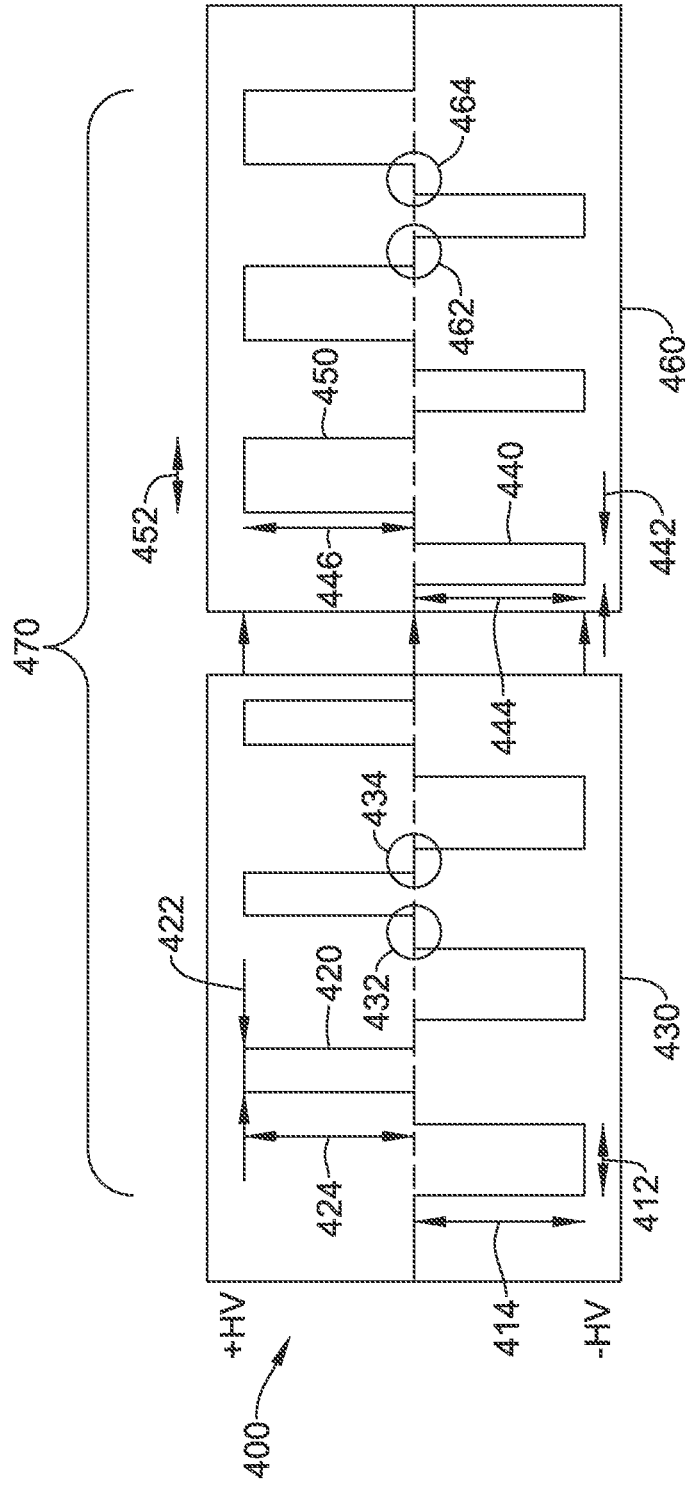
FIG. 11 shows an illustrative time multiplexed therapy output.

FIG. 11 shows an illustrative therapy waveform. This
example shows a method of delivering a multiphasic abla-
tion waveform comprising generating a first pulse train 430
comprising first pulses 410 of a first polarity (negative, in the
illustration) having a first amplitude 414 and a first pulse
width 412, alternating with second pulses 420 of a second
polarity opposite the first polarity, having a second ampli-
tude 424 and having a second pulse width 422 less than the
first pulse width 412. The example further includes gener-
ating a second pulse train 460 comprising third pulses 440
of the first polarity having a third amplitude 444 and a third
pulse width 442, alternating with fourth pulses 450 of the second polarity having a fourth amplitude 454 and a fourth pulse width 452 greater than the third pulse width 442. The example method may be performed such that the first pulse train 430 yields a first charge imbalance, and the second pulse train 460 yields a second charge imbalance that offsets the first charge imbalance to prevent muscle stimulation. The charge imbalance of the first pulse train 430 would be proportional to the difference between the product of amplitude 414, pulse width 412 and the quantity of first pulses 410 of the first pulse train 430, and the product of amplitude 424, pulse width 422, and the quantity of second pulses 420 of the first pulse train 430.

In some examples, the first and second amplitudes 414, 424 are the same, and the third and fourth amplitudes 444, 454 are the same. Further, the method may be performed such that a time 470 from the start of the first pulse train 430 to the end of the second pulse train 460 is short enough to avoid muscle stimulation due to the charge imbalance of the first pulse train 430. For example, time 470 may be shorter than one millisecond, or shorter than two milliseconds, or some other duration, as desired.

In some examples, the first and fourth pulse widths 412, 452 are equal in duration, and the second and third pulse widths 422, 442 are equal in duration. For example, the first and fourth pulse widths 412, 452 may be in the range of about 1 to about 20 microseconds, and the second and third pulse widths 422, 442 may be in the range of about 0.1 to about 10 microseconds. In some examples, the first pulse width 412 is about double the second pulse width 422, and the fourth pulse width 452 is about double the third pulse width 442. In other examples, the first, second, third and fourth pulse widths are each in a range of about 0.1 to 50 microseconds and may have other suitable ratios.

In general, the concept for FIG. 11 is to provide two pulse trains, each of which would be imbalanced if delivered alone, with delivery taking place in a short enough period of time to achieve charge balance without muscle stimulation. In other examples a single pulse train with asymmetric outputs within the pulse train may be used instead.

In some examples, the first pulse train 430 comprises a first quantity of first pulses 410 and a second quantity of second pulses 420, and the second pulse train 460 comprises a third quantity of third pulses 440 and a fourth quantity of fourth pulses 450, wherein the first, second, third and fourth quantities are all equal. In some examples, the first, second, third and fourth amplitudes each exceed an irreversible electroporation threshold. As noted, the "threshold" may be in part dependent on pulse width as well as the distances between electrodes. In other examples, the first, second, third and fourth pulse widths are each in a range of about 0.1 to 50 microseconds.

In an alternative formulation, a pulsetrain 430 may comprise an odd number of pulses, such as pulses p1 to p5, each having the same amplitude, in which pulses p1, p3 and p5 are of the same polarity and each have a pulse width PW, while pulses p2 and p4 are of opposite polarity and each have pulse width 1.5×PW, which would yield a charge balanced output even though pulses delivered in each polarity are unequal in charge content. In another example, a pulsetrain 430 may comprise an odd number of pulses each having the same pulse width, such as pulses p1 to p5, in which pulses p1, p3, and p5 are of the same polarity and each have an amplitude V, while pulses p2 and p4 are of opposite polarity and each have an amplitude 1.5×V, again providing an asymmetric output that, upon conclusion of the pulse train, is also charge balanced. Additional examples that build off of, or show alternatives to, FIG. 11, can be found in U.S.

Provisional Patent Application 62/819,120, filed Mar. 15, 2019, titled TIME MULTIPLEXED WAVEFORM FOR SELECTIVE CELL ABLATION, the disclosure of which is incorporated herein by reference.

Figure 12:
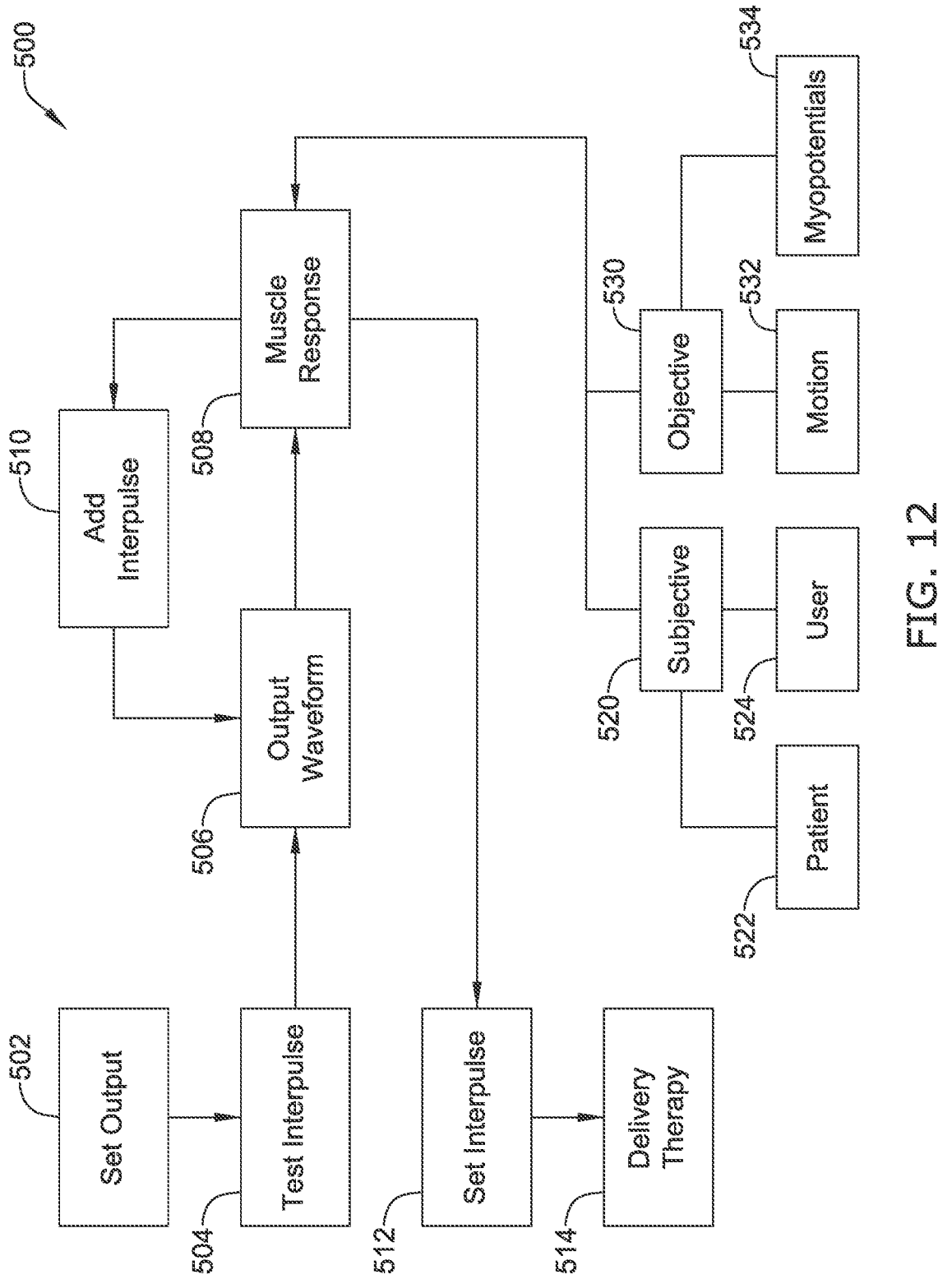
FIG. 12 shows a method for configuring and/or testing a therapy.

FIG. 12 shows a method for configuring and/or testing a therapy. An output configuration is set at 502. An output configuration may be, for example, definition of a therapy or non-therapy waveform to be delivered to a patient. A non-therapy waveform may be one which uses lower amplitude or a different pulse width than may be used during therapy, for example. For purposes of the method of FIG. 12, the non-therapy waveform—or therapy waveform, may be defined with a longer pulse width than would otherwise be used in therapy in order to amplify the effect of the waveform on patient muscle tissue, if desired. In the example, the output configuration 502 comprises at least first and second signal portions that are separated by an interpulse interval. As part of the output configuration an interpulse interval between two signals of opposing or different polarity can be set.

Next, the interpulse interval is tested as indicated at 504. Testing comprises delivering or outputting the waveform that was configured in 502, as indicated at 506, and then determining or observing whether a muscle response occurs 508. If no muscle response occurs, the method adds to the duration of the interpulse delay, as indicated at 510, and returns to block 506 to again deliver or output the waveform. The procedure is repeated in this example until one of two conditions is met—either a maximum or upper threshold interpulse interval is used, without any muscle response being observed, or a muscle response is observed. The aim is to maximize the interpulse interval in order to provide a therapy waveform that mimics a monophasic waveform, preferentially enhancing efficacy in causing cell death, while avoiding the side effect of muscle stimulation.

The interpulse delay can then be set, as indicated at 512. For example, the interpulse delay may be set by reducing the last interpulse delay which was tested by some margin or percentage, for example, by 1 to 50 microseconds, or by a percentage such as 5 to 25 percent. In some examples, the setting of the interpulse at 512 is performed differently depending on the nature of the end of testing at block 508, that is, if testing ends because the maximum interpulse is met without a muscle response, then the interpulse delay can be set to the maximum, or if the testing ends because of observed muscle response, the interpulse delay is set to a duration that is a reduction of the last tested interpulse, using a margin or percentage.

With the interpulse delay set at block 512, the method then proceeds to therapy delivery at 514. Therapy delivery may use the same or different parameters in terms of waveform shape, duration, amplitude or type as that tested in blocks 506/508. For example, because the aim in blocks 502 to 508 is to select an interpulse delay, which is largely a function of the surrounding tissue and not necessarily a function of the ablation target, it may not be necessary to perform testing using the parameters needed for ablation, which could confound the test results. In other examples, the interpulse delay is tested as part of therapy delivery itself, by using the actual ablation parameters in a repetitive series while adjusting the interpulse delays. In still further examples, as therapy is applied at block 514, for example, in a repeating series of pulse trains, muscle response may be monitored over time and, if muscle response is observed, the interpulse delay parameter may be modified, such as by reducing interpulse delay.

The step of monitoring for muscle response at 508 may use subjective and/or objective measurements or observations. For example, subjective monitoring 520 may include querying the patient 522 as to whether the patient is feeling any sensation of muscle tightening, twitching or the like, and/or asking if the patient is feeling other sensations such as tingling, buzzing, burning, paresthesia, etc. Subjective monitoring 520 may also be based on user or physician observation as indicated at 524, requesting that the user indicate whether motion, tightness or other physical response has been witnessed. In still other examples, objective measures 530 may be used including, for example, having a motion sensor 532 on a probe or placed in or on a patient at a relevant position to determine whether any motion—whether perceptible or not to the user or a patient, is taking place.

In some examples, muscle response may be observed by capturing electrical signals from the muscle itself (myopotentials 534); as muscle demonstrates an electrical response it would be understood that motion is imminent or likely to take place. Such signals can be captured using electrodes on a probe that is also used for therapy delivery, or on a separate device including those for cutaneous placement. In still other examples, during a therapy session, it may be that a gross observation—that is, patient sensation or motion—is used during setting of the interpulse delay, and myopotentials are used to provide feedback during therapy by determining whether electrical signals from the muscle change over time; increasing amplitude of sensed electrical response of the muscle may be used to reduce interpulse delay, or some other feature such as amplitude, to avoid triggering muscle motion; conversely, decreasing electrical response may indicate that changes in the ablated tissue (as cells are destroyed, for example) are reducing the likelihood of muscle response, allowing longer interpulse delay and/or higher amplitude outputs.

Figure 13A:
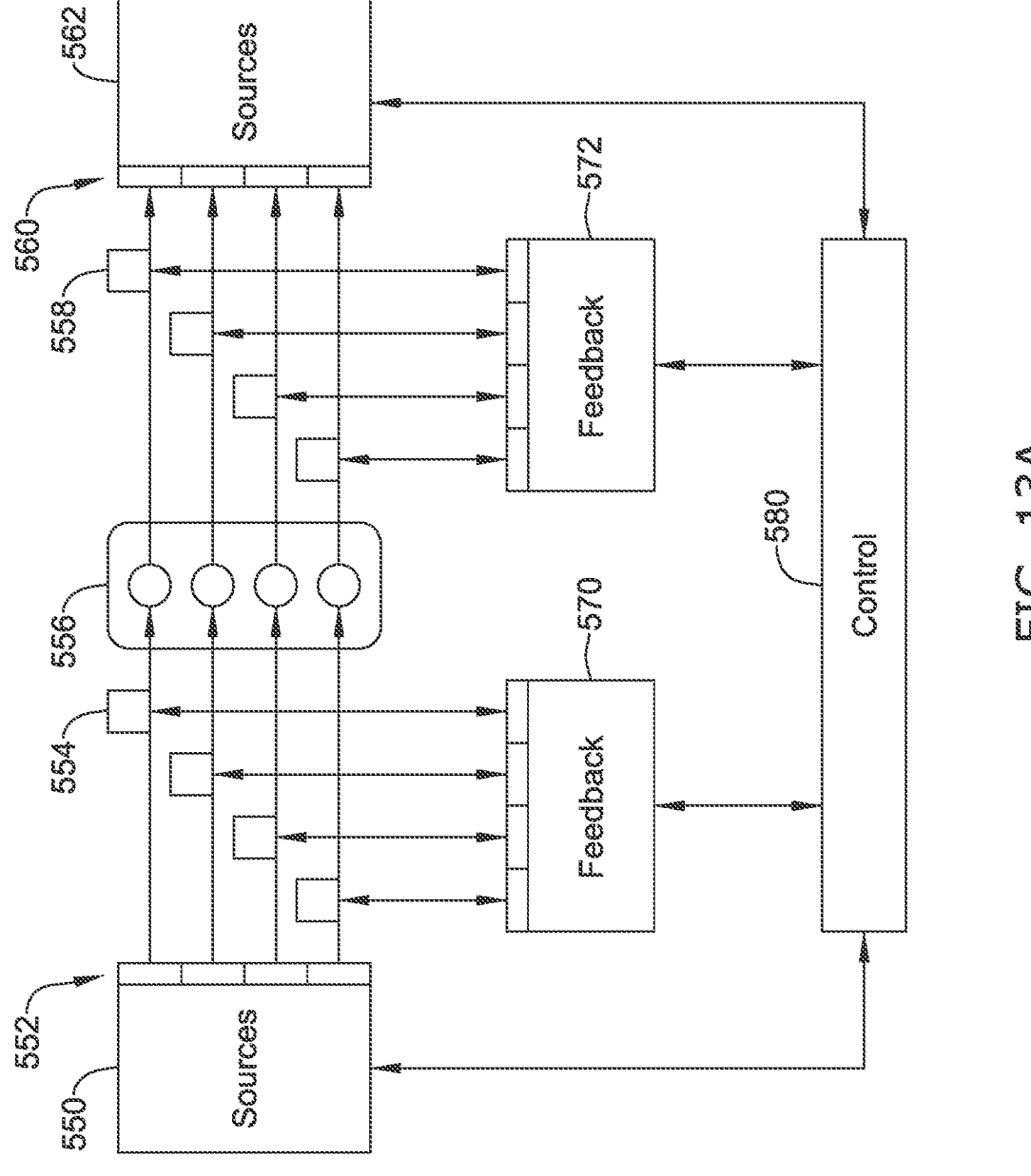

FIGS. 13A-13D show illustrative output and feedback circuits for a signal generator. Referring now to FIG. 13A, an illustrative example may comprise a plurality of sources 550, coupled to a plurality of switches 552 which allow multiple independent channels for ablative therapy to be delivered. The plurality of sources may comprise current sources (such as a set of current mirrors which can be summed together as desired), or may comprise plural voltage sources, such as a capacitor stack as illustrated further below in FIGS. 14A-14B. Depending on the nature of the sources 550, the switches 552 may be omitted as, for example, if current sources that can be independently disabled are used.

The conduction lines between the sources 550 and the output block 556 can be considered the "high side" of the output circuit in some examples. The high side conduction lines may be monitored if desired using feedback couplings indicated at 554. A feedback coupling 554 may be, for example, a current sensor for measuring current through the conduction line or a voltage sensor for measuring voltage. The above noted list of examples for voltage or current sensors may be used. Both a current sensor and a voltage sensor may be provided, if desired. The feedback coupling 554 is coupled to a feedback monitoring circuit 570, which may include, for example, various conditioning, filtering, comparing, sampling and/or storing circuits or circuit elements to capture what happens during a therapy output.

The output block 556 may include one or more mechanical ports, plugs or other coupling for mechanical and electrical connection to a therapy delivery probe. While four outputs are shown at 556, it should be understood that the invention is not so limited and any number of outputs may be provided. Two or more output blocks 556 may be provided instead, if needed.

Another set of conduction lines couples the output block 556 to another set of switches 560. Switches 560 may enable or disable an output and may link the outputs to a reference or ground for the system, or may couple to a plurality of sources 562. In some examples, ablation stimulus output may be simply coupled to system ground for return purposes. In other examples, one or more voltage or current sources may be used as a negative or sink for output energy, if desired.

The conduction lines between block 556 and switches 560 may be considered the low side conduction lines in some examples. An additional set of feedback couplings 558 may be provided on the low side conduction lines. The feedback couplings 558 may comprise voltage or current sensors, or both, as desired, and are again coupled to a feedback monitoring circuit 572, which may be similar to block 570. The high side sources 550 and switches 552, feedback circuits 570, 572, and low side sources 562 and switches 560 are all shown as coupled to the control block 580, which may include the various control elements discussed above relative to block 202 of FIG. 9.

The feedback monitoring circuits 570, 572 may be used to monitor peak current of delivered stimuli in order to identify overcurrent conditions and prevent componentry internal to the device from being harmed by overcurrent. Alternatively, peak or average current may be monitored to determine what the output is likely doing in the tissue, whether causing thermal or non-thermal ablation, for example. In an example, average current is monitored, referenced to a time block, such as by reference to the start and end point of a therapy phase, phases, or pulse train. Average current can be used to monitor for changing physiology as, for example, may be relevant to determining that electroporation is occurring and cell contents are being emptied into the intercellular fluid. In other examples, current feedback may be used to provide a current controlled output.

As noted above, additional feedback may be obtained as well from the probe used for stimulus/therapy delivery, including, for example, thermal sensing, acoustic sensing, visual observation/sensing, ultrasound, and impedance monitoring. Such feedback loops may be used to identify hazards and/or to monitor progress and/or success or failure of the therapy output to ablate tissue.

Figure 13B:
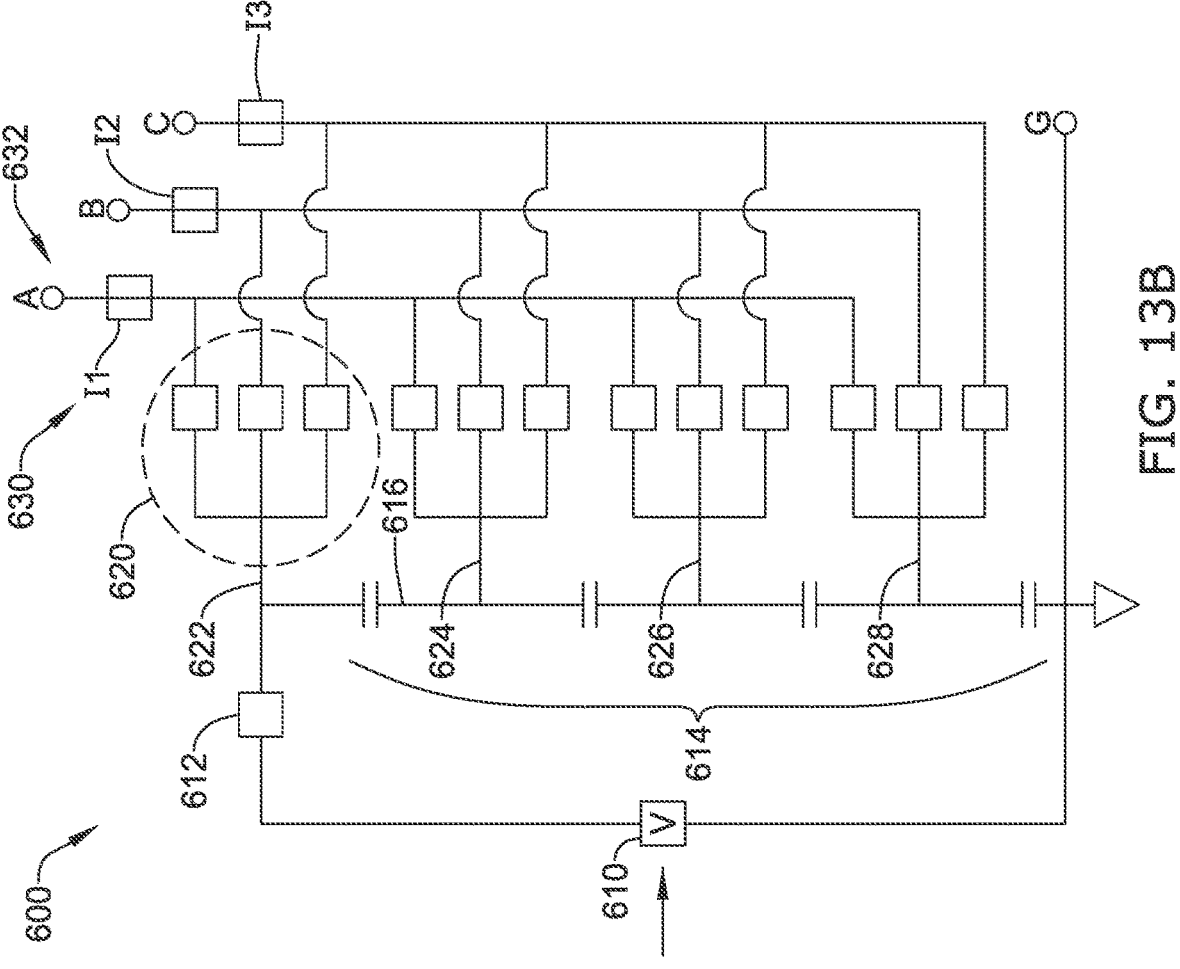

FIG. 13B shows another example for coupling a power source to a set of voltage sources (a capacitor stack), with independent outputs available at a plurality of different levels. The example 600 uses a voltage or power input 610 which is coupled to a step-up converter 612 that is used to charge a capacitor stack 614. Block 612 may be similar to block 212 of FIG. 9.

The example shows four capacitors 616 in the capacitor stack 614; any suitable number of capacitors can be used for examples using a capacitor stack, for example, from 2 to 20 capacitors, or more, as desired. The capacitors 616 and capacitor stack 614 collectively will be sized to allow the delivery of high voltage (kilovolt or higher) outputs of durations up to the millisecond range into loads as small as tens of ohms without significant drop-off in voltage. For example, typical output voltages may range between 200 volts to 10 kv, or lower or higher, and representative loads may be less than 10 ohms, such as 5 ohms or 2 ohms, or lower or higher. Representative capacitor sizes may be in the range of 10 to 10,000 microfarads, or lower or higher, either for individual capacitors or for the entire stack. A reconfigurable capacitor stack may include capacitors capable of being charged in parallel and discharged in series, or both charged and discharged in series or parallel using any suitable quantity and arrangement of switches and diodes to couple the capacitors together.

In an illustrative numeric example, the time constant of the output circuit, taking into account output circuit impedance (including the patient) of about 25 ohms, is preferably greater than 1 millisecond, and more preferably greater than 10 milliseconds. Thus, and for example, a set of four 1600 microfarad capacitors may be used, giving a stack capacitance of 400 microfarads, which would yield a 10 millisecond time constant when used with a 25 ohm load. Reducing the load to 10 ohms would still provide a time constant of 4 milliseconds. A larger load of course would provide a longer time constant. Other design parameters may be used, including different capacitor quantities and sizes, different patient load estimates, and a different target minimum time constant.

Sets of switch arrays 620 are coupled to nodes within the capacitor stack 614 at several different levels including at the top 622, between the top two capacitors 624, between the middle two capacitors 626 and between the lowest two capacitors 628. Each switch array separately defines paths A, B and C as selectable outputs that are each capable of tapping the stack at different power/voltage levels; each set 620 has one switch dedicated to each output path. As indicated at 630, each of the output paths may include a current monitor I1, I2, I3; in other examples a voltage monitor may be on each path, or both voltage and current may be monitored. The switches may be, for example, relays, high power mosfets, silicon controlled rectifiers (SCR), other transistors, or may include multi-part switches combining for example, an SCR for enabling a signal with a mosfet to turn the signal off. A ground or reference node G is highlighted as well.

As can be appreciated by the skilled artisan, FIG. 13B shows an example with multiple, independently operable channels. Given appropriately sized capacitors each channel generally can operate without affecting other channels. The size of the capacitors may be reflected in ratings of the output of the system as capacitor size, combined with output impedance (including the patient), can be used in combination to determine maximum pulse width and voltage/amplitude ratings. For example, if tapping the capacitor stack at position 626, the maximum output current (or minimum impedance) may be relatively larger than if tapping the capacitor stack at the top 622.

The topology shown omits various diodes and current control apparatuses that may be used to allow capacitor stack charging without directly linking step up voltages from block 612 to the actual outputs. In some examples, rather than a single coupling at 612 to the top of the capacitor stack, voltage conversion may use a multiple-tapped transformer, with each tap tied to a node 622, 624, 626, 628, effectively charging the capacitor stack in parallel while allowing series discharge. For charging, a primary phase would load the transformer with energy from the voltage source 610, and a secondary phase would discharge the loaded energy into the capacitor stack 614. Whichever of the capacitors carries the least voltage would be charged to the greatest extent during the secondary phase. Appropriately timing the secondary phase would allow charging of the capacitor stack intermittent with therapeutic output. By using a multi-tap charging circuit, the capacitor stack can be refreshed and rebalanced as current is drawn from selected portions thereof.

Figure 13C:
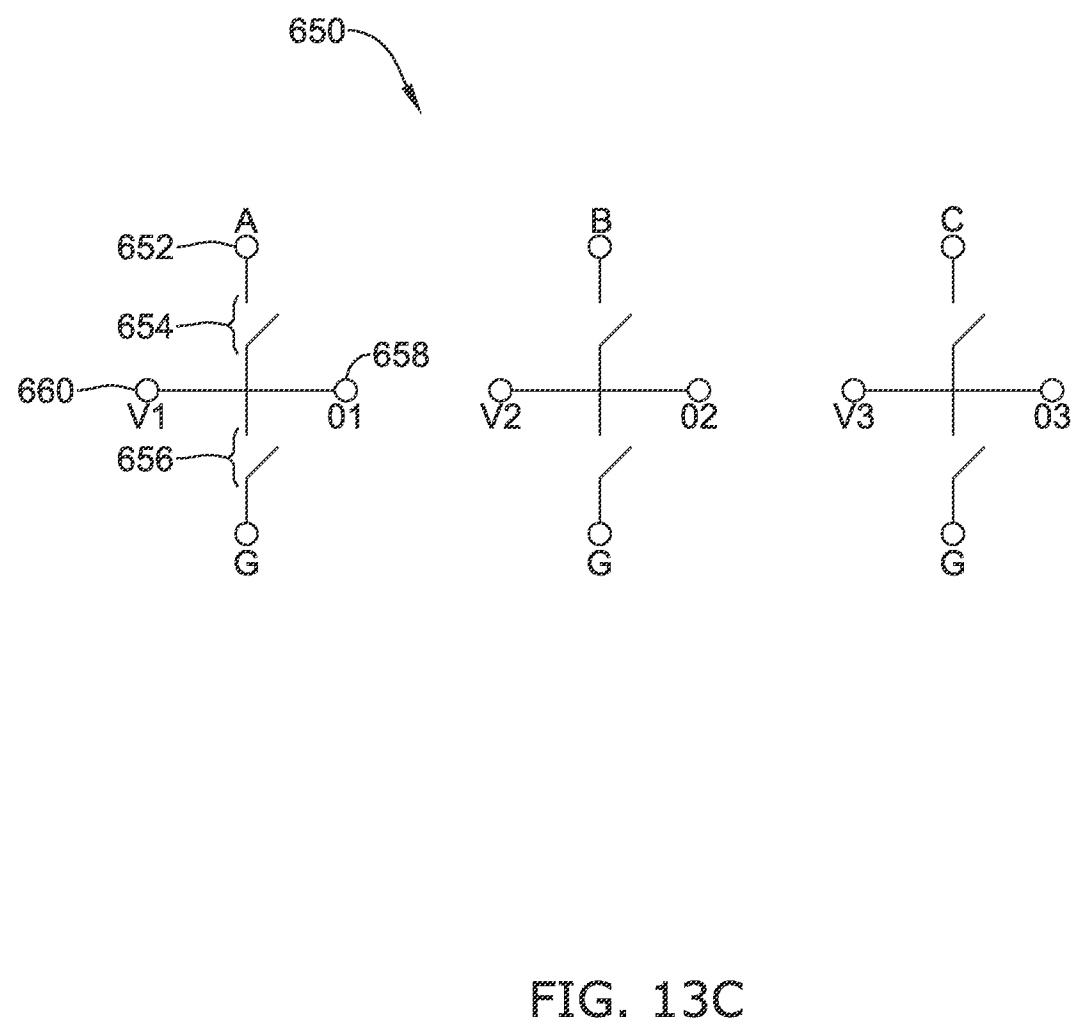

FIG. 13C shows an illustrative output configuration. Reusing the A, B, C denominations from FIG. 13B, a set of output nodes O1, O2, O3 is shown coupled to outputs A, B, C. Switch 654 couples node A of the circuit in FIG. 13B to the output node O1 658. Switch 654 is to some extent redundant, noting that the switches shown in FIG. 13B within each group 620 could be the sole switches. While two switches may add complexity, it also may limit leakage current which could be harmful to the patient. Indeed, in some examples one switch may be an enable switch while the other is used to aid in wave shaping and/or to cut off current flow. Current and/or voltage may be measured using node 660. A grounding switch is shown at 656. During operation, the grounding switch 656 may be used to define a return electrode for an output—that is, any output current may be delivered relative to ground. As noted previously, rather than a ground or reference, the return may instead be to a negative voltage source or to a current sink, if desired.

Figure 13D:
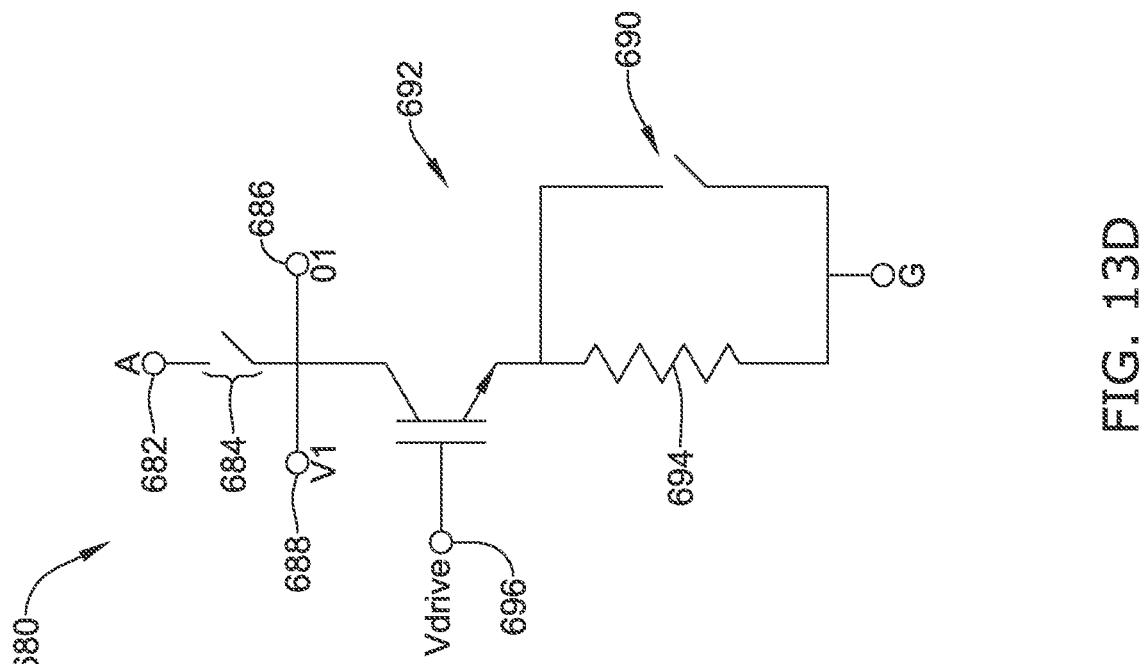

FIG. 13D shows an alternative configuration which allows an output node to be placed in either voltage or current controlled operation. The circuit 680 is shown for coupling a single node A 682 to output O1 686, but may be replicated for a plurality of output nodes. A first switch 696 connects the output O1 to a resistor 694 and bypass switch 690. For a voltage controlled output, switch 690 and transistor 696 are simultaneously closed. Opening switch 690 while driving transistor 696 routes current through the resistor 694. By controlling VDrive, powering transistor 696, the current passing through the circuit can be controlled, since the current through resistor 694 is limited by the equation: VDrive>I×R(694), where R(694) is the resistance of resistor 694, and I is the current. The configuration is somewhat similar to that shown in U.S. Pat. No. 6,952, 608, where it was used to deliver constant current pacing stimulus in an implantable defibrillator. Other configurations may be used as are known in the art.

In some examples, current control can be performed using a current controlling circuit as in FIG. 13D. In other examples monitoring circuitry, whether on the high side, low side, or at the input/output circuitry, can be used to monitor voltage and/or current. Then, analog to digital conversion circuitry or other regulators may be used to modify the return reference voltage or the output voltage taken from the capacitor stack to change voltage output and provide a constant current, constant voltage, or constant power (power being the product of voltage and current) output. For example, as current changes are measured and monitored, voltage output may be increased or decreased to maintain constant power. In another example, a constant power circuitry may control current flow as shown in FIG. 13D, while monitoring output voltage, and may modify the current flow by adjusting the VDrive signal to ensure that the product of current and voltage delivered to the probe is constant.

Figure 14A:
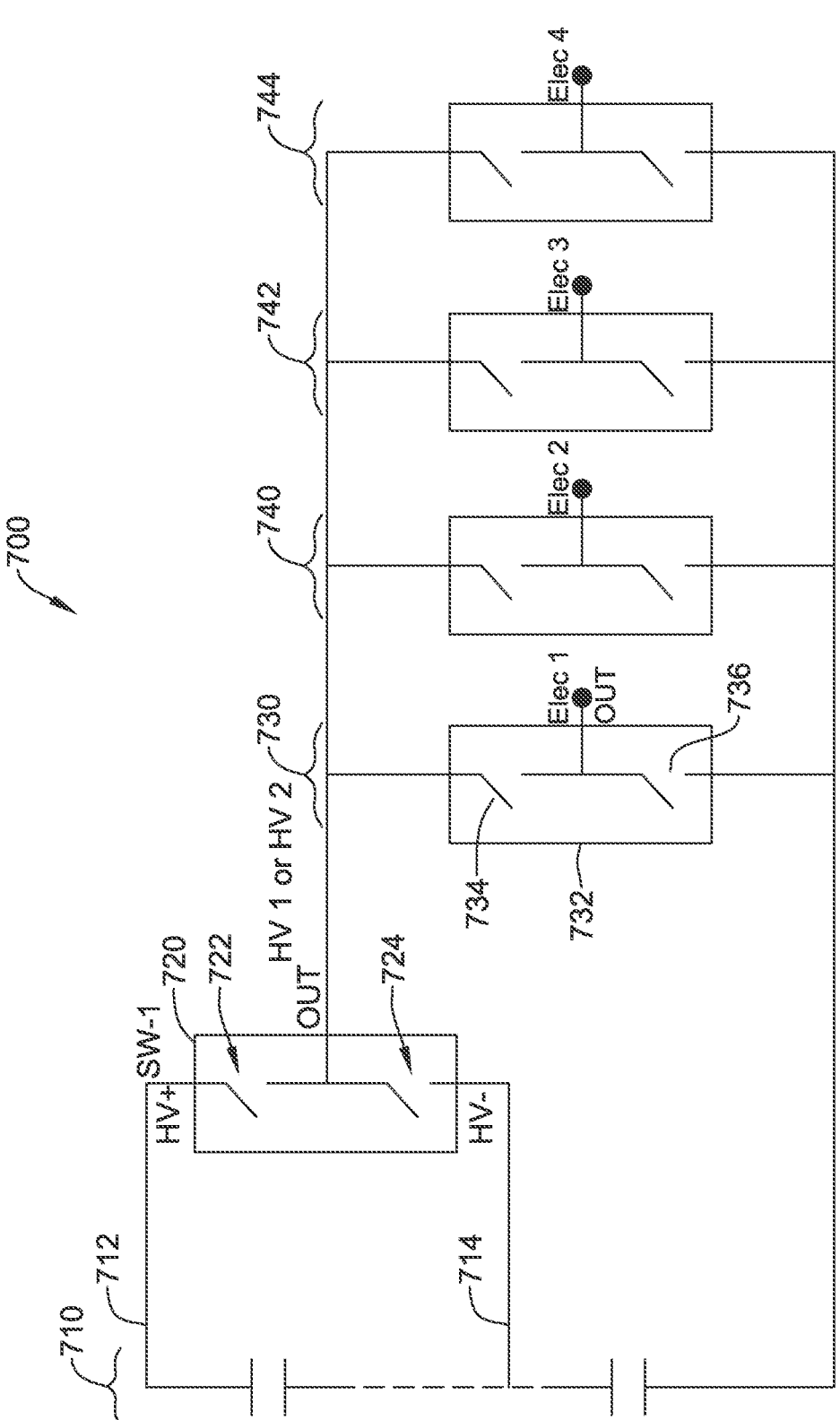
FIGS. 14A-14B show illustrative pulse generation circuits.
Figure 14B:
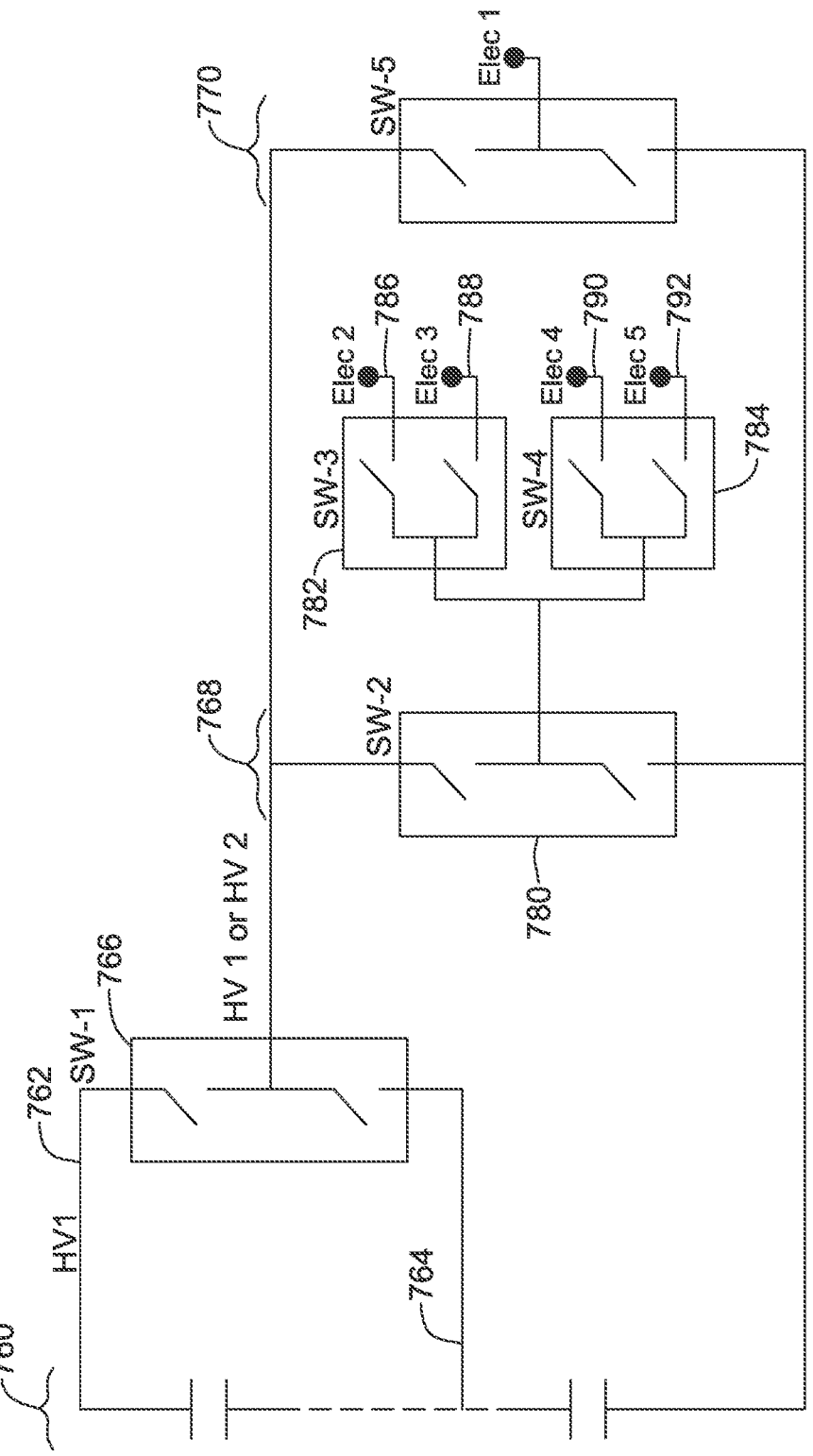

FIGS. 14A-14B show illustrative pulse generation circuits. Referring now to FIG. 14A, the circuit 700 comprises a capacitor bank or stack shown at 710, having a plurality of capacitors and a number of circuit paths, including at least paths 712, 714 exiting it. The capacitor stack 710 can be charged using a voltage source (not shown), which may be a battery or a line voltage, as desired, coupled to a voltage convertor to generate voltages in the range of one to several kilovolts; 2, 4, 6 and up to 10 kilovolts, or more, may be used.

An output stage is then provided including at least one power selector switch pair, shown at 720. The power selector switch pair 720 is shown having first and second switches 722, 724 which enable selection of all or only a portion of the capacitor stack to power an output signal. More than two switches may be included to enable a plurality of different power levels to be selected if desired. If switch 722 is closed while switch 724 is open, a higher voltage output can be chosen using the entire capacitor stack 710, while if switch 722 is open and switch 724 is closed, a lower voltage output can be chosen by using less than the entire capacitor stack, thereby excluding at least one of the capacitors of the capacitor stack.

The output circuit further includes a plurality of output arms 730, 740, 742, 744, each including an electrode selector switch pair. The electrode selector switch pairs control which of the output nodes, marked here as Elec1, Elec2, Elec3, and Elec4, is active as anode or cathode. Two or more such nodes may be active as anodes or cathodes at once; for example, there may be one anode, one cathode, and two open nodes, or two anodes and one cathode with one open node, or two cathodes and one anode with one open node, or two cathodes and two anodes, etc., in various combinations. Each electrode selector switch pair includes a high side switch coupled to the power selector switch pair and a low side switch coupled to a reference. For example, electrode switch pair 732 has a high side switch 734 for coupling to the power selector 720, and a low side switch 736 for coupling to a reference or system ground. If desired, additional branches may include discharge and/or leak resistors (not shown) allowing for active or passive discharge of the circuit when not in use.

FIG. 14B shows another topology. This time, the capacitor stack or bank 760 is connected by at least two output paths 762, 764 to a power selector 766 as in FIG. 14A. Electrode switch pairs in this example include at least first and second overall branches 768, 770. While switch pair 770 is similar to the switch pairs shown in FIG. 14A, switch branch 768 is different. A first switch pair 780 enables access to a plurality of lower level branches with switch pairs 782, 784 allowing selective coupling to a set of four output nodes 786, 788, 790, 792. Thus a plurality of topologies of varying complexity may be used to allow separate selection of both power level (via block 766) as well as the outputs to be used (via branches 768, 770).

Figure 15:
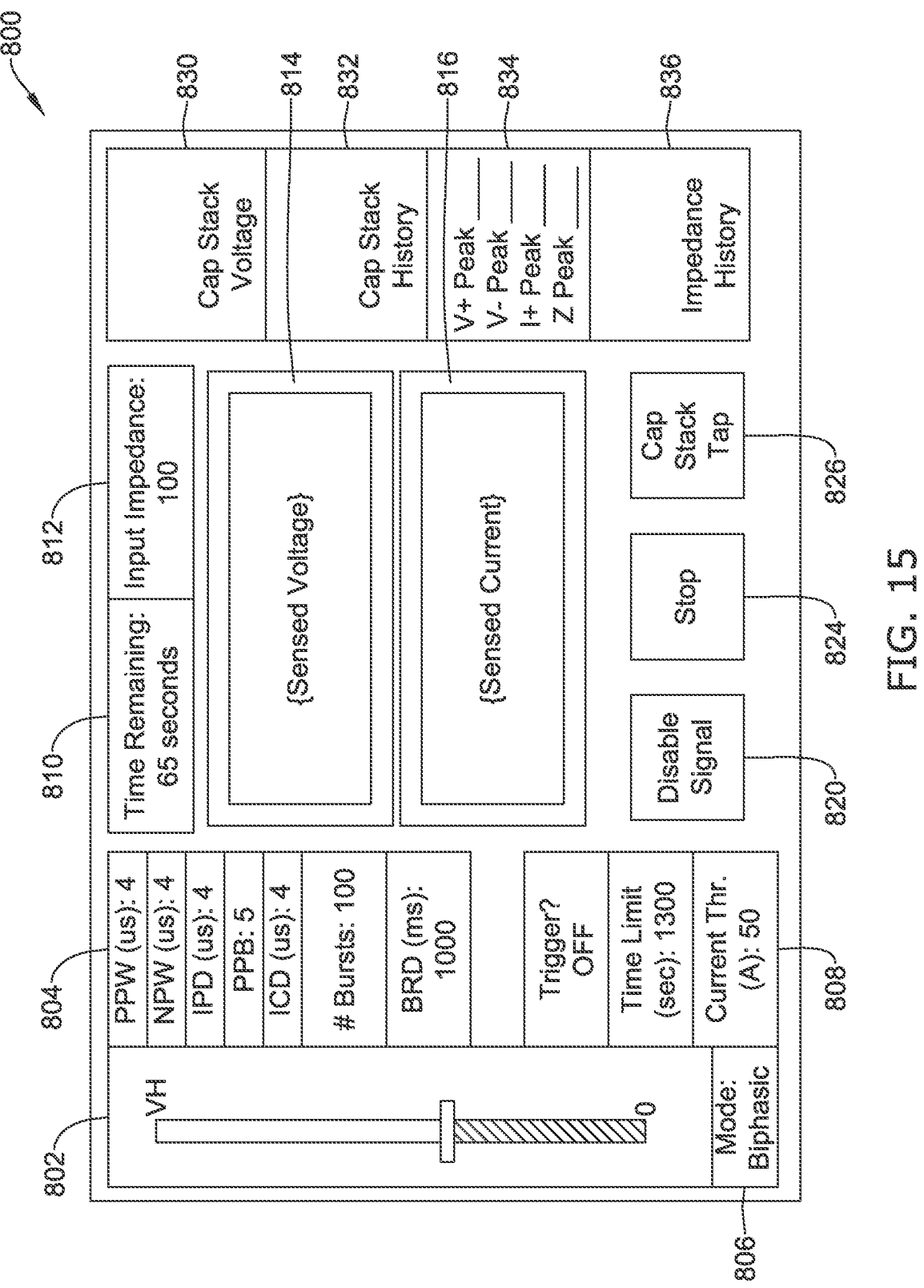
FIG. 15 shows an illustrative user interface.

FIG. 15 shows an illustrative user interface. The user interface may be generated on a display screen, such as on a stand-alone screen, a laptop computer, a tablet computer, or any other suitable device. The display screen may be a touch screen. The display 800 shows a broad variety of features and diagnostics for the user. A slider bar is shown at 802 for displaying, relative to a maximum voltage (VH), the current output maximum amplitude; the user may modify the current output maximum amplitude via touchscreen, rollerball, mouse, touchpad, keyboard, etc. A number of current settings are shown at 804 including positive pulse width (PPW), negative pulse width (NPW), and interpulse duration (IPD). Each of PPW, NPW, and IPD may be modified using the various embodiments shown herein as well as using the embodiments shown in related U.S. Provisional Patent Applications 62/819,120, and 62/819,135, the disclosures of which are incorporated herein by reference.

Additional modifiable parameters include the pulses per burst (PPB), which controls how many pulses are delivered in a single burst of ablation energy. The intercycle delay (ICD) defines how much time will pass between two sets of pulses. The number of bursts to be delivered (# Bursts) can also be set, as well as the delay between bursts (BRD). In the example shown, output energy would be delivered as four microsecond positive and negative square waves with a four microsecond delay between the two square waves, with five pairs of positive and negative square waves delivered (PPB) having four microseconds between the end of a negative square wave and the succeeding start of a positive square wave. Each burst of 5 cycles is separated from the next burst by 1000 milliseconds, and one-hundred bursts are to be delivered.

Additional control features are shown at 808, with a trigger set to off. If the trigger is on, a biological feature, such as an identified reference point in a cardiac cycle, may be used to trigger each burst, rather than the BRD. In an alternative, having the trigger on, with a BRD set, may indicate that each burst is to be separated from the next by at least the BRD, with a new burst triggered by a sensed biological feature such as the cardiac cycle reference point. A cardiac cycle reference point may be, for example, the identification of an R-wave or QRS complex, which may be followed by some post-event delay. For example, a triggered output may be delivered by sensing an R-wave and waiting 5 to 100 milliseconds for the end of the R-wave before therapy delivery, with the above noted goal of finishing the burst before the T-wave occurs. The system may be set up to automatically calculate a delay by subtracting from a known, tested, or estimated S-T duration the length of time needed to complete a burst, if desired.

The additional features 808 may also define a time limit for completing the therapy, which could timeout to prevent system hang-up. A current threshold is set as noted as well and may be provided to ensure that current does not exceed a threshold that could present a risk of harm to the patient. For example, it is known that as cells are ablated local impedance may drop; excess current could lead to heating of tissue or damage to components, so setting a limit may be useful to ensure safety or to control spatial characteristics of the ablation effects.

As indicated at 810, a time remaining indicator can be provided, as well as a measurement of impedance 812. Impedance may be reported as an overall impedance for the system output, including impedance of the probe being used, or may be more particular to the impedance of the patient tissue being treated.

Graphs may be displayed showing sensed output voltage waveforms 814, overall or for particular or recent cycles or bursts of therapy output. Sensed current may similarly be shown in graphical form 816.

A disable signal button 820 may be provided to allow pre- or post-therapy display of one or more patient signals; during therapy delivery this button 820 may be greyed out, hidden or inaccessible if desired. A stop button is displayed prominently at 824 to allow therapy to be turned off whenever needed. Current settings for using levels of the capacitor stack may be displayed at 826.

Further diagnostics and statuses are shown at the right side of the display, including a current capacitor stack voltage at 830, history of the capacitor stack voltage at 832, and peak sensed voltages for positive and negative phases of the output signal as well as peak current (positive is indicated but negative could be as well), and peak impedance calculation may be displayed in the block at 834. The history of impedance can be shown on a graph relative to time in the block at 836.

The particular set of parameters and diagnostics shown is merely exemplary, and more, less or different parameters and diagnostics may be shown. The organization of the display may be modified if desired as well.

Figure 16A:
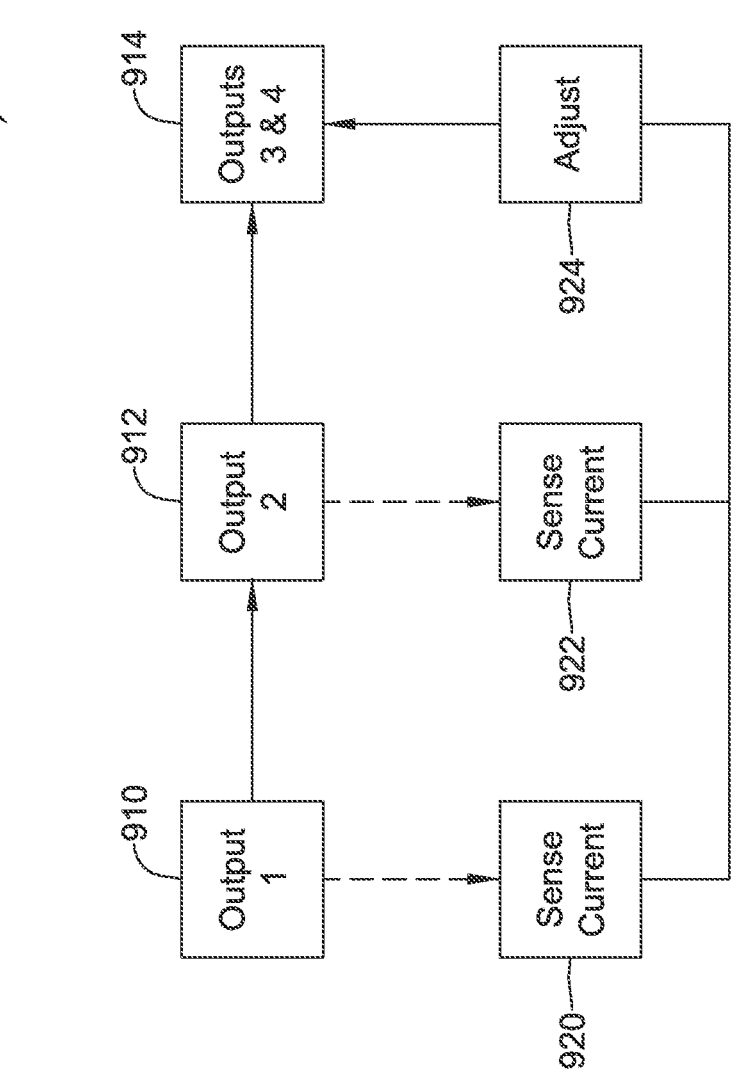
FIGS. 16A-16B show a method for therapy delivery that uses unbalanced waveforms with correction of detected charge imbalance, the method shown in block and graphical form.
Figure 16B:
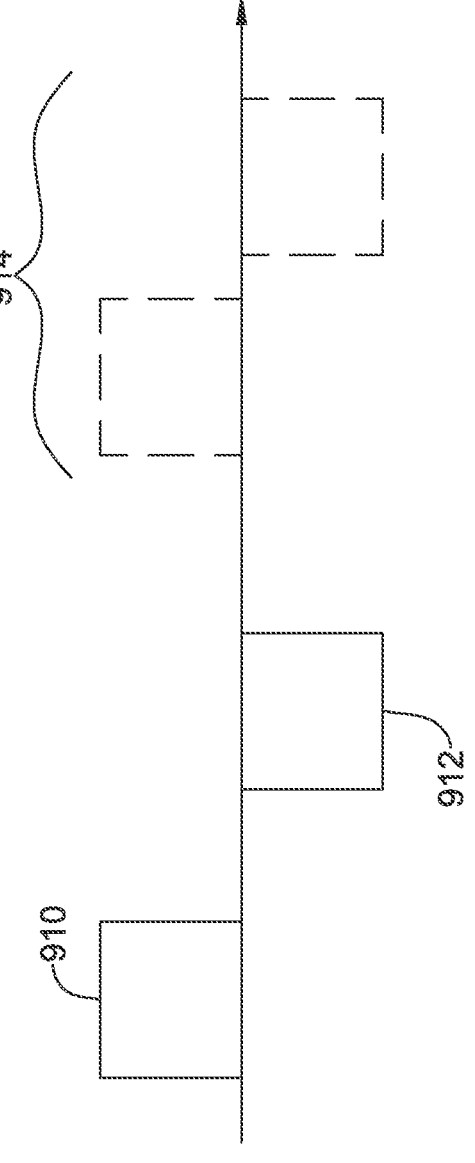

FIGS. 16A-16B show a method for therapy delivery that uses unbalanced waveforms with correction of detected charge imbalance. FIG. 16A shows the method in block form, while FIG. 16B shows the method in a graphical format. Starting with the FIG. 16A, the figure illustrates a method of delivering an ablation therapy to a patient comprising delivering a therapy pulse train within a predetermined period of time. The method includes delivering a first output at 910. The first output may be a first pulse having first voltage and first duration. The method includes sensing at least current during the first pulse, as indicated at 920.

Next, the method comprises delivering a second output as indicated at 912. The second output may include a second pulse having second voltage and duration. In an example, the first voltage does not equal the second voltage, and the first duration does not equal the second duration, but the product of the first voltage and first duration is substantially equal to the product of the second voltage and the second duration. Further the method comprises sensing current during the second pulse, as indicated at 922.

The method then includes making an adjustment, as indicated at 924, to the charge balance that results from the first and second outputs 910, 912. In an example, the adjustment 924 comprises determining that a quantity of charge delivered during the first pulse is not equal to a quantity of charge delivered during the second pulse. The adjustment comprises delivering at least one additional pulse to remove charge imbalance caused by difference between the quantity of charge of the first pulse and the quantity of charge of the second pulse, before expiration of the predetermined period of time. The one additional pulse may include a single output or more than one output, as indicated at 914.

FIG. 16B shows the method in graphic form, as a first pulse 910 is delivered having a first amplitude and first pulse width, and a second pulse 912 is delivered with a second amplitude and second pulse width. The height and width of the two pulses 910, 912 can be seen to be different, but the area beneath the line for the two pulses is approximately equal—that is, generally speaking, equal to within about +/−10%, or +/−5%, or +/−2%. While that combination of voltage and duration may be expected to provide a balanced output in terms of charge, in the real world this may not be the case. Therefore one or more adjustment pulses are delivered at 914.

In further examples, the at least one additional pulse is a voltage controlled pulse having a third voltage and a third duration calculated by determining an impedance encountered by at least one of the first and second pulses. Alternatively, a total charge delivered during the first and second pulses, or net charge delivered in the first and second pulses, may be calculated. In another example, the adjustment pulse(s) 914 may be delivered as current controlled outputs, while the initially delivered pulses 910, 912, may be delivered as voltage controlled outputs. The adjustment pulses may be delivered at a non-therapy amplitude or duration, if desired.

Rather than single pulses, the operation may be to perform a burst of any number of pulses while tracking total charge delivered, followed by one or more corrective outputs to negate charge imbalance. While a significant charge imbalance may not necessarily occur from a single cycle within a burst, or even from a single burst, the concern may be that over time, as cycles are repeated within bursts, and bursts are repeated within a therapy plan, the charge imbalance could build up to become significant enough that it affects the patient or therapy by, for example, causing muscle stimulation. Thus adjustments may be made after pairs of outputs, after cycles, after bursts, or occasionally within a series of bursts. For example, correction may be periodic and provided after a set number of cycles or bursts, or after a set period of time, or may be occasional and provided when a sensed or calculated imbalance reaches or crosses a threshold.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. Implementations of methods may include code, such as microcode, assembly language, a higher-level language, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable disks, magnetic cassettes, memory cards or sticks, random access memories (RAMs), read only memories (ROMs), and the like. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of treating a patient using an ablation therapy comprising:

setting output parameters for a biphasic electrical output comprising a first phase of a first polarity and a second phase of a second polarity opposite the first polarity, with an interpulse period defined between the first and second phases;

a) delivering the biphasic electrical output to the patient using the output parameters and observing whether a muscle response occurs;

b) if no muscle response is observed, modifying the output parameters by extending the interpulse period defined between the first and second phases;

repeating steps a) and b) until a muscle response is observed or until a predefined maximum interpulse period is used; and if a muscle response is observed, setting a therapeutic interpulse period as either a fraction of or a reduction of the interpulse period at which muscle response is observed; or if the maximum interpulse period is used, setting the therapeutic interpulse period at the maximum interpulse period; and delivering therapy to the patient using a set of therapy parameters including the therapeutic interpulse period.

2. The method of claim 1, wherein the step of observing whether a muscle response occurs is performed by a system user visually observing whether one of visible motion or migration of therapy probe occurs in response to the delivered biphasic electrical output.

3. The method of claim 1, wherein the step of observing whether a muscle response occurs is performed by monitoring an output of an accelerometer placed in or on the patient.

4. The method of claim 3 wherein the step of delivering the biphasic electrical output to the patient is performed using a probe, and the accelerometer is on the probe.

5. The method of claim 1, wherein the step of observing whether a muscle response occurs includes sensing myopotentials of muscle tissue of the patient.

6. The method of claim 5 wherein the step of delivering the biphasic electrical output to the patient is performed using a probe, and the step of sensing myopotentials of muscle tissue of the patient is performed using one or more electrodes on the probe.

7. The method of claim 1, wherein the step of observing whether a muscle response occurs comprises obtaining a subjective feedback from the patient.

8. A method of treating a patient using an ablation therapy comprising:

setting output parameters for a biphasic electrical output comprising a first phase of a first polarity and a second phase of a second polarity opposite the first polarity, with an interpulse period defined between the first and second phases;

delivering the biphasic electrical output to the patient using the output parameters;

observing whether a muscle response occurs;

a) if no muscle response is observed, modifying the output parameters by extending the interpulse period defined between the first and second phases;

b) if a muscle response is observed, modifying the output parameters by reducing the interpulse period defined between the first and second phases; and again delivering the biphasic electrical output to the patient using the output parameters as modified in one of steps a) and b).

9. The method of claim 8, wherein the step of observing whether a muscle response occurs is performed by a system user visually observing whether one of visible motion or migration of therapy probe occurs in response to the delivered biphasic electrical output.

10. The method of claim 8, wherein the step of observing whether a muscle response occurs is performed by monitoring an output of an accelerometer placed in or on the patient.

11. The method of claim 8, wherein the step of observing whether a muscle response occurs includes sensing myopotentials of muscle tissue of the patient.

12. The method of claim 11 wherein the step of delivering the biphasic electrical output to the patient is performed using a probe, and the step of sensing myopotentials of muscle tissue of the patient is performed using one or more electrodes on the probe.

13. The method of claim 8, wherein the step of observing whether a muscle response occurs comprises obtaining a subjective feedback from the patient.

14. An ablation device for generating energy for use in electrical ablation of tissue comprising:

a voltage source;

a capacitor bank for storing energy from the voltage source to be used in delivery ablation therapy;

an output stage coupling the capacitor bank to a plurality of output nodes;

sensing circuitry for receiving a sensed signal from a probe adapted for use with the ablation device; and a control circuit configured to control the capacitor bank and output stage, using feedback from the sensing circuitry, wherein the control circuitry is configured to perform a method of treating a patient using an ablation therapy comprising:

setting output parameters for a biphasic electrical output comprising a first phase of a first polarity and a second phase of a second polarity opposite the first polarity, with an interpulse period defined between the first and second phases;

a) delivering the biphasic electrical output to the patient using the output parameters and observing whether a muscle response occurs;

b) if no muscle response is observed, modifying the output parameters by extending the interpulse period defined between the first and second phases;

repeating steps a) and b) until a muscle response is observed or until a predefined maximum interpulse period is used; and if a muscle response is observed, setting a therapeutic interpulse period as either a fraction of or a reduction of the interpulse period at which muscle response is observed; or if the maximum interpulse period is used, setting the therapeutic interpulse period at the maximum interpulse period; and delivering therapy to the patient using a set of therapy parameters including the therapeutic interpulse period.

15. The ablation device of claim 14, wherein the control circuit is further configured to observe whether a muscle response occurs by obtaining an input from a system user who visually determines whether one of visible motion or migration of therapy probe occurs in response to the delivered biphasic electrical output.

16. The ablation device of claim 14, wherein the control circuit is further configured to observe whether a muscle response occurs is performed by monitoring an output of an accelerometer located in or on the patient.

17. The ablation device of claim 16, wherein the control circuit is further configured to deliver the biphasic electrical output to the patient via a probe coupled to the ablation device, and the accelerometer is on the probe.

18. The ablation device of claim 14, wherein the control circuit is further configured to observe whether a muscle response occurs by sensing myopotentials of muscle tissue of the patient.

19. The ablation device of claim 18, wherein the control circuit is configured to deliver the biphasic electrical output to the patient via a probe, and to sense myopotentials of muscle tissue of the patient using one or more electrodes on the probe.

20. The ablation device of claim 14, wherein the control circuit is further configured to observe whether a muscle response occurs by obtaining an input from a user relating to subjective feedback from the patient.

\* \* \* \* \*